United States Patent
Connolly et al.

(10) Patent No.: US 11,752,339 B2
(45) Date of Patent: Sep. 12, 2023

(54) METHODS AND SYSTEMS FOR STIMULATING NERVE SIGNALS

(71) Applicant: SRI International, Menlo Park, CA (US)

(72) Inventors: Christopher Connolly, Menlo Park, CA (US); Patrick Lincoln, Menlo Park, CA (US); Maneesh Yadav, Menlo Park, CA (US); John Cornwell, Menlo Park, CA (US); Bhaskar Ramamurthy, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 587 days.

(21) Appl. No.: 15/608,872

(22) Filed: May 30, 2017

(65) Prior Publication Data
US 2017/0340881 A1 Nov. 30, 2017

Related U.S. Application Data

(60) Provisional application No. 62/450,478, filed on Jan. 25, 2017, provisional application No. 62/342,402, filed on May 27, 2016.

(51) Int. Cl.
*A61N 1/36* (2006.01)
*A61F 2/72* (2006.01)
*A61B 5/24* (2021.01)
*A61B 5/00* (2006.01)
*G16H 50/50* (2018.01)
*G16H 40/63* (2018.01)
(Continued)

(52) U.S. Cl.
CPC ............ *A61N 1/3605* (2013.01); *A61B 5/24* (2021.01); *A61B 5/4029* (2013.01); *A61F 2/72* (2013.01);
(Continued)

(58) Field of Classification Search
CPC ..... A61B 5/04; A61B 5/04001; A61B 5/4029; A61B 5/4836; A61B 5/24; A61N 1/3605; A61N 1/36053; A61N 1/3606; A61F 2/72
See application file for complete search history.

(56) References Cited

U.S. PATENT DOCUMENTS

2003/0144710 A1* 7/2003 Haugland .......... A61B 5/04001
607/48
2005/0021103 A1 1/2005 Dilorenzo
(Continued)

FOREIGN PATENT DOCUMENTS

| JP | 2008538994 A | 5/2013 |
| JP | 2013528416 A | 3/2015 |
| WO | WO 2008/134197 A2 | 11/2008 |

OTHER PUBLICATIONS

Dietrich S, Smith J, Scherzinger C, et al. A novel transcutaneous vagus nerve stimulation leads to brainstem and cerebral activations measured by functional MRI. Biomed Tech (Berl) 2008;53: 104-111.
(Continued)

*Primary Examiner* — Pamela M. Bays
(74) *Attorney, Agent, or Firm* — Rutan and Tucker, LLP

(57) ABSTRACT

Systems and methods of generating and applying a synthetic neuromodulatory signal are described. A subject may be put under a particular condition that causes an effect in the subject. While the subject is under the condition, a recording of neurogram signals derived from the condition can be made from the subject. For example, neuronal signals traveling on the vagus nerve of the subject may be monitored and recorded. The neurogram may then be used to create a synthetic neuromodulatory signal that can be administered to a user. When the synthetic neuromodulatory signal is administered to the user, the user may experience the same effect as the subject that had been placed in the condition,
(Continued)

even though the user was never put under the same condition.

12 Claims, 21 Drawing Sheets

(51) Int. Cl.
    *G16H 40/67*     (2018.01)
    *G16H 20/10*     (2018.01)
    *G16H 20/70*     (2018.01)

(52) U.S. Cl.
    CPC .......... *A61N 1/3606* (2013.01); *A61B 5/4836* (2013.01); *A61B 2503/40* (2013.01); *A61N 1/36053* (2013.01); *G16H 20/10* (2018.01); *G16H 20/70* (2018.01); *G16H 40/63* (2018.01); *G16H 40/67* (2018.01); *G16H 50/50* (2018.01)

(56) References Cited

U.S. PATENT DOCUMENTS

| | | | |
|---|---|---|---|
| 2005/0283198 | A1 | 12/2005 | Haubrich et al. |
| 2006/0020297 | A1 | 1/2006 | Gerber et al. |
| 2006/0142802 | A1 | 6/2006 | Armstrong |
| 2006/0241697 | A1 | 10/2006 | Libbus |
| 2010/0125304 | A1* | 5/2010 | Faltys ................ A61N 1/36053 607/2 |
| 2013/0238050 | A1* | 9/2013 | Simon .................... A61N 2/006 607/42 |
| 2013/0245486 | A1 | 9/2013 | Simon et al. |
| 2014/0067005 | A1* | 3/2014 | Kaula .................... G16H 50/50 607/46 |
| 2014/0236257 | A1 | 8/2014 | Parker et al. |
| 2014/0336722 | A1 | 11/2014 | Rocon De Lima et al. |
| 2015/0134026 | A1 | 5/2015 | Kaula et al. |
| 2015/0163604 | A1 | 6/2015 | Fruhauf et al. |
| 2016/0022995 | A1 | 1/2016 | Kothandaraman et al. |

OTHER PUBLICATIONS

Kevin J. Tracey, "Shock Medicine—Stimulation of the nervous system could replace drugs for inflammatory and autoimmune conditions," Scientific American (Mar. 2015).
Japanese Patent Office, Notice of Refusal dated Apr. 2, 2021, 6 pp.
European Patent Office, European Search Report and Written Opinion, PCT/US2017/046314, dated Jan. 8, 2020, 8 pp.

* cited by examiner

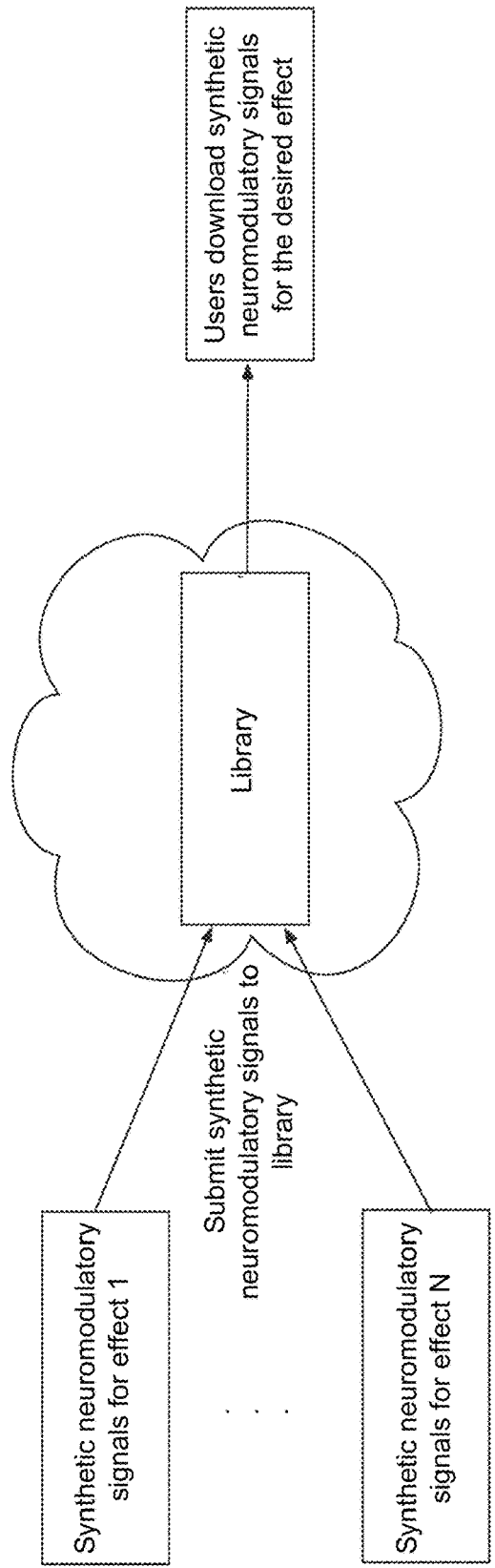
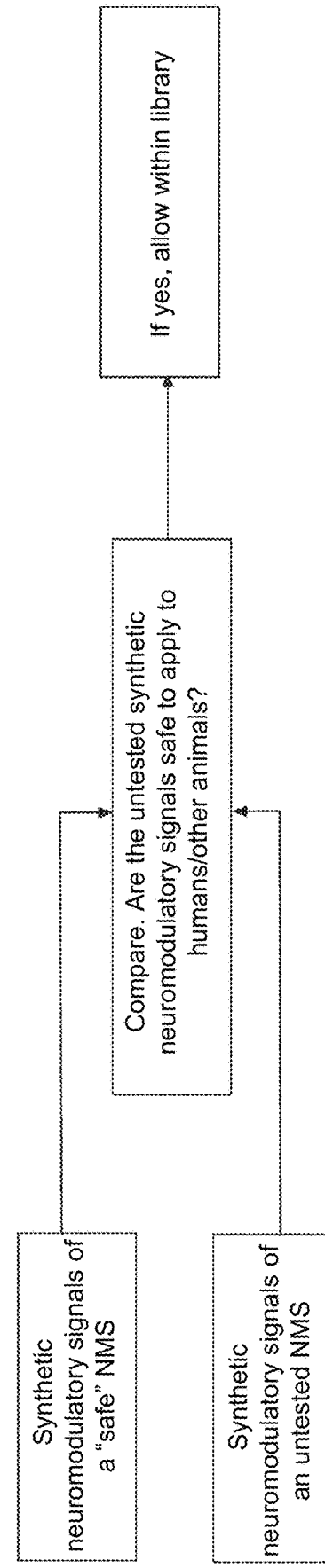
FIG. 8A
FIG. 8B

```
# OK, NDE exiting now. Here is a state description:
s1 duration=7.7148437e-05 amplitude=0.0,0.0 rate=0.0,0.0
s2 duration=4.8828125e-05 amplitude=0.5452198067055,0.2256273071115 rate=1.5,0.67412
s3 duration=1.4648437e-05 amplitude=0.8643667397196,0.0808568279852 rate=8.7,0.953389
s4 duration=1.3671875e-05 amplitude=0.9287458116996,0.1021049913089 rate=4.8,0.962231
s5 duration=9.1796875e-05 amplitude=0.9619652322816,0.0176372307693 rate=35.7,0.446154
s6 duration=3.5156250e-05 amplitude=0.9940167148246,0.0109583508985 rate=39.9,0.266495
s7 duration=0.0001054687 amplitude=0.8724513848368,0.0023534913507 rate=55.8,0.155649
s8 duration=0.0001689453125 amplitude=0.6358506391556,0.0015746913835 rate=64.2,0.119456
s9 duration=0.0005146484375 amplitude=0.4807976712276,0.0014937536252 rate=62.1,0.095984
s10 duration=0.000324221875 amplitude=0.4760032597359,0.0017901584975 rate=54.6,0.117431
s11 duration=0.0002890625 amplitude=0.6069792313316,0.0019250962518 rate=38.7,0.178743
s12 duration=0.00024023437 amplitude=0.6301854212516,0.0021593280110 rate=27.9,0.299995
s13 duration=0.00016210937 amplitude=0.6495921616456,0.0029005957224 rate=16.5,0.463152
s14 duration=0.00017675781 amplitude=0.6896925885388,0.0070821413313 rate=3.9,0.381266
s15 duration=3.515625e-05 amplitude=0.1905735599758,0.01 rate=0.3,0.001 s1 s2 duration=0.0001132812
s2 s3 duration=7.03125e-05
s3 s4 duration=7.03125e-05
s4 s5 duration=0.0003173828125
s5 s6 duration=2.8320312e-05
s6 s7 duration=0.00021875
s7 s8 duration=0.00044433593
s8 s9 duration=0.00119921875
s9 s10 duration=0.0010576171875
s10 s11 duration=0.0015087890625
s11 s12 duration=0.0007753906
s12 s13 duration=0.0002392578125
s13 s14 duration=0.000253906
s14 s15 duration=7.7148437e-05
```

*FIG. 15*

METHODS AND SYSTEMS FOR STIMULATING NERVE SIGNALS

RELATED APPLICATIONS

The present application claims priority under 35 U.S.C. 119(b) to PCT Application No. PCT/US2017/034863 filed on May 26, 2017 in the English language. This application also claims priority under 35 U.S.C. § 119(e) to U.S. Provisional Application No. 62/342,402, entitled "A METHOD FOR COMPILING AND SYNTHESIZING STIMULATION SIGNALS FOR VAGUS-BASED SOMATIC CONTROL," filed on May 27, 2016; and U.S. Provisional Application No. 62/450,478, entitled "MODULATION OF NERVOUS SYSTEM SIGNALS," filed on Jan. 25, 2017; the content of each of these related applications is hereby incorporated by reference in their entireties.

BACKGROUND

Field

This disclosure relates generally to methods, devices and systems for stimulating nerve signals. More specifically, this disclosure relates to technologies for processing measured peripheral nerve tissue signals into synthetic neuromodulatory signals (NMS), distributing representations of the synthetic neuromodulatory signals, and applying the generated synthetic neuromodulatory signals to subjects for various applications, including providing personalized therapeutic benefits.

Description of the Related Art

There is one vagus nerve on each side of the human body. The vagus nerve is a major component of the autonomic nervous system and plays an important role in the regulation of metabolic homeostasis.

Implantable devices have been used to stimulate the left cervical vagus nerve as a treatment for varying conditions, such as epilepsy and depression. These devices are typically implanted through surgery by subcutaneously placing a generator in the upper chest of a patient. An electrode lead is then attached from the generator to the vagus nerve. Devices for stimulating the right cervical vagus nerve have been used to treat heart failure, as one example.

Transcutaneous devices have also been used to stimulate the auricular branch of the vagus nerve (ABVN) by targeting the cutaneous receptive field of the ABVN. Applying an electrical signal, as compared to an acoustic signal, to the left cymba conchae that is above the sensory threshold, but below the pain threshold, has resulted in brain activation that is not dissimilar to that of the left cervical ventral nerve stimulation. See Dietrich S, Smith J, Scherzinger C, et al. *A novel transcutaneous vagus nerve stimulation leads to brainstem and cerebral activations measured by functional MRI*. Biomed Tech (Berl) 2008; 53:104-111.

SUMMARY

Disclosed herein are systems, devices, and methods for modulating nervous system signals.

One embodiment is a system for applying a neuromodulatory signal to a user, comprising: neuromodulatory signal generator system comprising a plurality of synthetic neuromodulatory signals, wherein each synthetic neuromodulatory signal represents at least one processed measured peripheral nerve tissue signal as a sequence of one or more states represented by one or more state parameters; and an electronic device communicating with the neuromodulatory signal generator system, wherein the electronic device comprises:

a user interface configured to receive a selection of at least one desired effect from the user;

a communication module to receive the selection of the at least one desired effect from the user interface and connect to the neuromodulatory signal generation system to retrieve a synthetic neuromodulatory signal associated with the selected desired effect, wherein application of the retrieved synthetic neuromodulatory signal to the user causes the user to experience the desired effect without application of a drug to the user.

Another embodiment is a method of retrieving a synthetic neuromodulatory signal to be administered to a user, comprising: receiving a selection of a desired effect from a user interface of an electronic device; downloading a first synthetic neuromodulatory signal associated with the desired effect to the electronic device in response to the selection; and receiving an input of operational parameters from the user interface relating to application of the downloaded first synthetic neuromodulatory signal.

Still another embodiment is a non-transient computer readable medium containing instructions that when executed perform a method comprising: receiving a selection of a desired effect from a user interface of an electronic device; downloading a first synthetic neuromodulatory signal associated with the desired effect to the electronic device in response to the selection; and receiving an input of operational parameters from the user interface relating to application of the downloaded first synthetic neuromodulatory signal.

One additional embodiment is a neuromodulatory signal generator system for converting one or more measured peripheral nerve tissue signals to a neuromodulatory signal that may be applied to a user, comprising: a storage module comprising the one or more measured peripheral nerve tissue signals taken from a subject subjected to a condition; a processing module communicating with the storage module to receive at least one of the one or more measured peripheral nerve tissue signals and configured to process the at least one measured peripheral nerve tissue signal; a state machine generator module communicating with the processing module to receive the at least one processed measured peripheral nerve tissue signal and configured to create a synthetic neuromodulatory signal, the synthetic neuromodulatory signal created by representing at least one of the processed measured peripheral nerve tissue signals as a sequence of one or more states wherein each state is represented by one or more state parameters that are converted to the synthetic neuromodulatory signal; and a communication module to send the synthetic neuromodulatory signal to a device that is configured to apply the synthetic neuromodulatory signal to the user, wherein application of the synthetic neuromodulatory signal to the user causes the user to experience a desired effect without application of the condition to the user.

One other embodiment is a method for converting one or more measured peripheral nerve tissue signals to a neuromodulatory signal that may be applied to a user, comprising: receiving at least one measured peripheral nerve tissue signal taken from a subject subjected to a condition; creating a synthetic neuromodulatory signal by representing at least one of the measured peripheral nerve tissue signals as a sequence of one or more states wherein each state is represented by one or more state parameters that are converted to the synthetic neuromodulatory signal; and sending the synthetic neuromodulatory signal to a device configured to apply the synthetic neuromodulatory signal to a user, wherein application of the synthetic neuromodulatory signal to the user causes the user to experience a desired effect without application of the condition to the user.

One embodiment is a non-transient computer readable medium containing instructions that when executed perform a method comprising: receiving at least one peripheral nerve tissue signal taken from at least one subject subjected to a condition; creating a synthetic neuromodulatory signal by representing at least one of the peripheral nerve tissue signals as a sequence of one or more states and wherein each state is represented by one or more state parameters; and sending the synthetic neuromodulatory signal to a device configured to apply the synthetic neuromodulatory signal to a user; wherein application of the synthetic neuromodulatory signal to the user causes the user to experience a desired effect without application of the condition to the user.

Another embodiment is an electronic device for generating a neuromodulatory signal that may be applied to a user, comprising: a user interface configured to receive a selection of at least one desired effect from the user; a communication module to receive the selection from the user interface and connect to a remote neuromodulatory signal generation system to communicate the selection and receive 1) a first representation of at least one neuromodulatory signal associated with the selection and 2) a set of parameters related to the selection; and a neuromodulatory signal generation module to receive the first representation of the at least one neuromodulatory signal and configured to generate a second representation of the at least one neuromodulatory signal that is based on the first representation, the second representation to be applied to the user; wherein application of the second representation of the neuromodulatory signal to the user causes the user to experience a desired effect without application of a drug to the user.

One additional embodiment is a method for generating a representation of a neuromodulatory signal, comprising: receiving a selection of at least one desired effect from a user; connecting to a neuromodulatory signal generation system to communicate the selection and receive 1) a first representation of at least one neuromodulatory signal associated with the selection and 2) a set of operational parameters related to the selection; receiving the first representation of the at least one neuromodulatory signal; and generating a second representation of the at least one neuromodulatory signal that is based on the first representation, the second representation to be applied to the user, wherein application of the second representation of the neuromodulatory signal to the user causes the user to experience a desired effect without application of a drug to the user.

An additional embodiment is a non-transient computer readable medium containing instructions that when executed perform a method comprising: receiving a selection of at least one desired effect from a user; connecting to a neuromodulatory signal generation system to communicate the selection and receive 1) a first representation of at least one neuromodulatory signal associated with the selection and 2) a set of operational parameters related to the selection; receiving the first representation of the at least one neuromodulatory signal; and generating a second representation of the at least one neuromodulatory signal that is based on the first representation, the second representation to be applied to the user, wherein application of the second representation of the neuromodulatory signal to the user causes the user to experience a desired effect without application of a drug to the user.

BRIEF DESCRIPTION OF THE DRAWINGS

FIG. 8A is a schematic diagram of a synthetic neuromodulatory signals library into which NMS parameters may be submitted.

FIG. 8B is a flow diagram of a method to test for safety of a neuromodulatory signal.

FIG. 15 shows one embodiment of an exemplary state machine file.

DETAILED DESCRIPTION

Figure 1:
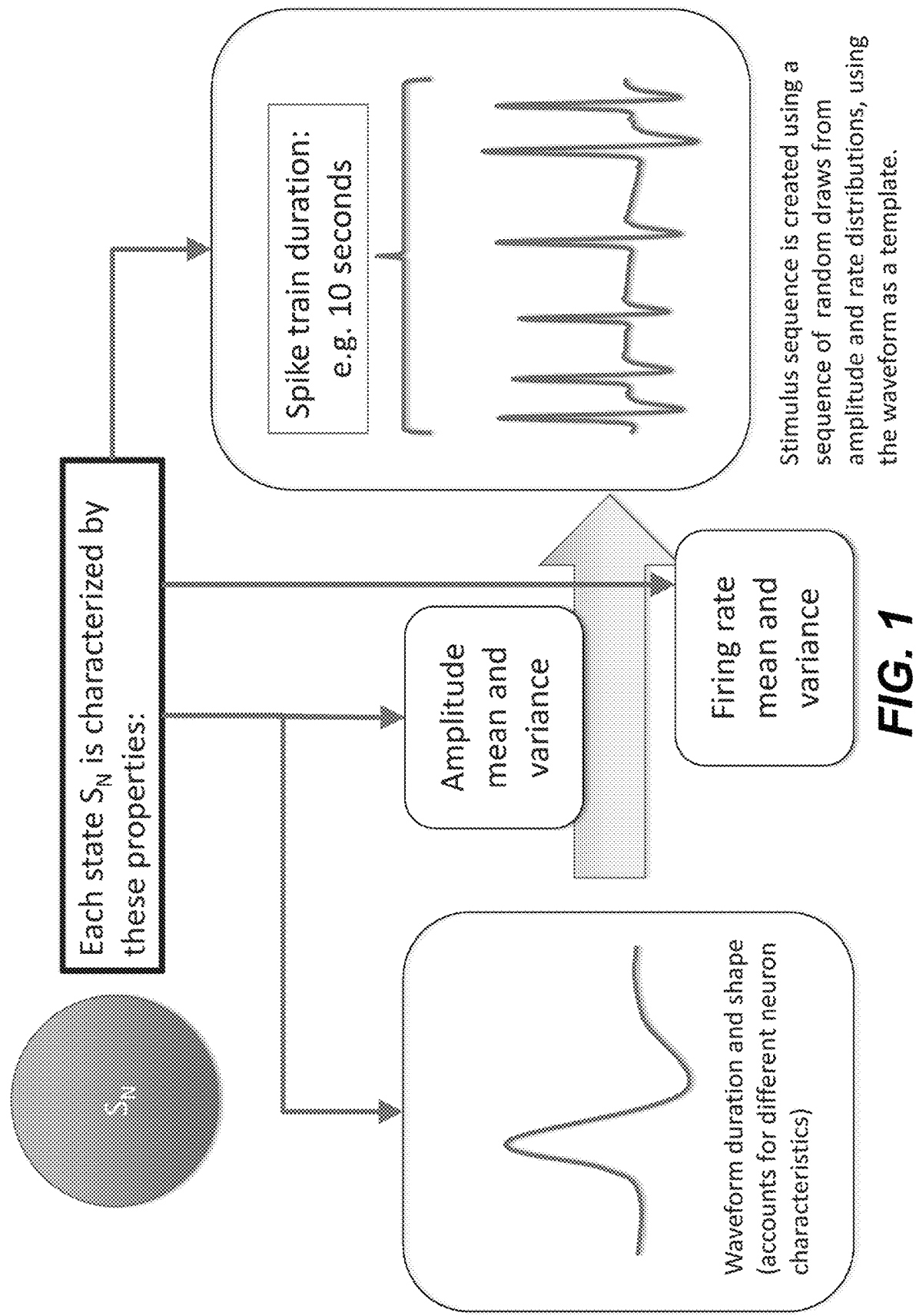
FIG. 1 is a data flow diagram showing that a "state" can be represented by some properties.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and databases referred to herein are incorporated by reference in their entirety with respect to the related technology.

Definitions

Unless defined otherwise, technical and scientific terms used herein have the same meaning as commonly understood by one of ordinary skill in the art to which the present disclosure belongs. For purposes of the present disclosure, the following terms are defined below.

As used herein, the term "stimulus" can refer to any stimulation of a nerve or the nervous system (e.g. a portion of the vagus nerve), whether electrical, mechanical, or otherwise. For example, a peripheral nerve of a subject can be stimulated. A peripheral nerve can be a nerve of the peripheral nervous system (PNS), which includes the somatic nervous system and the autonomic nervous system. The somatic nervous system includes the cranial nerves, except the optic nerve. Cranial nerves include the olfactory nerve, the optic nerve, the oculomotor nerve, the trochlear nerve, the abducens nerve, the trigeminal (ophthalmic) nerve, the trigeminal (maxillary) nerve, the trigeminal (mandibular) nerve, the facial nerve, the vestibulocochlear nerve, the glossopharyngeal nerve, the vagus nerve, the accessory nerve, and the hypoglossal nerve. The PNS system includes the brachial plexus nerve, the musculocutaneous nerves (such as the radial nerve, the median nerve, the ulnar nerve), the thoracoabdominal nerves (such as intercostals nerve, the subcostal nerve, the iliohypogastric nerve, the lateral cutaneous nerve of the thigh, the genitofemoral nerve), the lumbar plexus nerves (such as the obturator nerve, the femoral nerve, the muscular branches of the femoral nerve, the saphenous nerve), and the sacral plexus nerves (such as sciatic nerve, the tibial nerve, the common peroneal nerve, the deep peroneal nerve, the superficial peroneal nerve, the sural nerve). A stimulation of a nerve may cause one or more neurons to fire at the same amplitude and timing as is indicated by a desired neurogram. The nervous system stimulation maybe effectuated by electrical or mechanical stimulations, or by other means (such as light stimulations).

As used herein, the term "neurogram" refers to a measurement of the signals that traverse a nerve. In one embodiment, the neurogram may be produced in response to application of a particular condition of a subject. It should be realized that use of the term "subject" as used herein includes any animal or human subject that is put under a condition and provides a neurogram. For example, the condition may be wherein the subject has been given a particular treatment, such as by administration of a drug. The condition may also be wherein the subject is in a particular circumstance, for example when the subject is hungry, tired, cold, warm, or any other circumstance but has not been treated with an external composition. One example of a neurogram includes a structured sequence of electrical neuronal spikes, where the sequence of electrical neuronal spikes has a characteristic amplitude envelope, an inter-spike interval profile and a definite extent in time (e.g., a defined time interval). A "neurogram" can be an electrical recording representing of the state of a peripheral nerve. A neurogram can be processed by, e.g., a finite state machine to generate synthetic neuromodulatory signals of a processed neurogram.

As used herein, the term "state machine" representation or "finite state machine" representation may refer to, e.g., a mathematical model or a numerical model of a stimulus. In some versions of the disclosed system, each state in the state machine representation corresponds to a set of parameters that dictate a known spike amplitude and timing interval. For example, a processed neurogram may have an associated set of synthetic neuromodulatory signals, such that application of the stimulus according to the set of parameters can result in the known or expected spike amplitude and timing.

Overview

Embodiments of the invention relate to systems and methods of stimulating nerves as an alternative to drug-based treatments of animals and human patients/users. As used herein, the term "user" may indicate 1) a person using the system to select and apply synthetic neuromodulatory signals—for example, a doctor or service provider, 2) the recipient of the synthetic neuromodulatory signals, 3) the subject of the measured peripheral nerve tissue signal (the neurogram). The user may also be a friend, family member or pharmacist. In some instances, the user that uses the system or is having a synthetic neuromodulatory signal administered may be the same person. In one embodiment, the system targets a nerve, such as the vagus nerve, by exciting the nerve using a specific stimulus. As described below, stimulation of the nervous system may be useful as a way to replace drug treatments for inflammatory and autoimmune conditions in a patient. Stimulation of a peripheral nerve or a tissue, such as the vagus nerve, can produce a variety of beneficial effects. These effects may be dependent on the specific stimulation patterns that are used when stimulating the nerve. In one embodiment, stimulation of the nerve can be based on prior electrophysiological recordings from the nerve being stimulated. In other embodiments, the electrophysiological recordings can be processed into synthetic neuromodulatory signals or descriptors. Stimulation of the nerve may be based on neuromodulatory signals generated based on NMS parameters. In other embodiments, stimulation of the nerve may be based on newly discovered stimulatory signals that were determined to have a beneficial effect on the patient. The systems, methods, and devices disclosed herein may enable generation of these stimulus patterns without requiring surgery, or prior recordings of nerve functions. The stimulation signals may be presented to an individual through a variety of means. For example, the stimulation signals may be presented through sound vibrations, light stimulation, other devices attached to the ear or eye that are configured to stimulate nerves, such as the vagus nerves, of the body.

Embodiments may provide a convenient, safe and effective way for the development and use of nervous system stimulation techniques. In some embodiments, the technologies described in this disclosure may provide personalized therapeutic benefits. In some embodiments, patients may be able to directly manage their individual health condition through an automated system, which may include a user-friendly human-computer interface, instructions implemented in software, and hardware including processor(s), memory, and input/output device(s). For example, one embodiment includes a repository of stimulatory signals, such as synthetic neuromodulatory signals. Each synthetic neuromodulatory signal can correspond to a specific pattern that has been correlated with a particular desired effect. For example, stored synthetic neuromodulatory signals for generating a NMS #1 may be useful to treat depression. A user could download the synthetic neuromodulatory signals from the repository for NMS #1, and load it into an electronic device with an applicator or directly onto an applicator device where the applicator (on the electronic device or stand-alone) is configured to stimulate his peripheral nerve, such as the vagus nerve. By playing the NMS #1 on his or her device, the user could be treated for depression without the need to resort to pharmaceutical medications. The repository may include stimulatory signals, as described below, for a variety of desired effects (such as decreasing appetite). The desired effects may be associated with stimulations of the vagus, or other, nerves in the body.

Some embodiments include an electronic system or device that creates a NMS by first obtaining recorded neurograms of nerve signals from a population of subjects (such as a test group), and applies the processed version of the neurogram in the form of NMS to one or more other individual users. In this context, the individuals may be an animal or human patient or user. For instance, one embodiment includes applying a stimulus to an individual, and then recording the resulting neurogram that comes from application of the stimulus. The neurogram may then be converted into one or more useful forms, such as, for example synthetic neuromodulatory signals. A NMS signal, such as an acoustic signal, a mechanical signal, an electrical signal, or an electromechanical signal, generated based on a synthetic neuromodulatory signals can be applied to a target animal or human patient or user. Converting the synthetic neuromodulatory signal into an acoustic or other signal may also involve performing signal to noise reduction processes, or other processes to modify the signal in the neurogram so that the resultant synthetic neuromodulatory signal can be used to generate an accurate NMS (such as an acoustic signal) that is more effective when administered to the target animal, human patient or other user. Methods and systems for enabling these technologies and its many variations are described in more detail below.

One example system can synthesize virtually any desired stimulation pattern using specification of a number of input parameters. The ability to "program" stimulus patterns benefits peripheral nerve or tissue stimulation therapy, such as vagus nerve stimulation therapy. Such stimulation therapy can be used therapeutically for conditions such as diabetes and epilepsy. Furthermore, such stimulation therapy can be used for inducing pro- and anti-inflammatory effects, and for enhancement of learning and memory as described in more detail below. In one embodiment the stimulation therapy is effective to provide anti-inflammation effects and/or pro-inflammation effects. In alternative embodiments, application of the NMS signals or signal can result in different types of effects.

The systems, methods, and devices can be used as an adjunct to increase the usefulness of any programmable nerve or tissue stimulation device. For example, one example system can be used to complement a signal generator to deliver waveforms at a desired rate and power. As another example, the method can process potential neurogram signals harvested by recording the neurogram signals directly from the vagus nerve of an anaesthetized subject that has been placed under one or more conditions that evoke a vagus nerve response.

One embodiment is system that applies a neuromodulatory signal to a user. The system includes two principle components. The first component is a neuromodulatory signal generator system that stores a plurality of synthetic neuromodulatory signals. Each synthetic neuromodulatory signal stored in the neuromodulatory signal generator system represents at least one processed measured peripheral nerve tissue signal. As indicated below, the processed measured peripheral nerve tissue signal may be a signal derived from a neurogram. The neurogram may have been recorded from a subject that had been put into a particular condition to cause a desired effect. For example, the subject may have been treated with a first drug to suppress the appetite of the subject. The recorded neurogram from the subject may be processed through a state machine, as discussed below, the form a sequence of one or more states represented by one or more state parameters. The second principle component of the system is an electronic device that communicates with the neuromodulatory signal generator system. In one embodiment, the electronic device is a portable electronic device. This communication may be through any conventional communication connections including local and wide-area networking connections such as the Internet. In one embodiment, the electronic device is a wireless telephone or other electronic device with a touchscreen having a user interface for input. The user interface on the electronic device may be configured to receive a selection of at least one desired effect from the user. For example, the user interface may present a listing of possible desired effects to the user. The user can touch at least one of the desired effects on the device touchscreen to select that effect. Once the user has selected the desired effect, a communication module in the electronic device receives the user's selection of at least one desired effect from the user interface. The connection module then connects to the neuromodulatory signal generation system to receive a particular synthetic neuromodulatory signal associated with the selected desired effect. The synthetic neuromodulatory signal received by the electronic device is one wherein application of the synthetic neuromodulatory signal to the user would cause the user to experience the desired effect without application of a drug to the user.

Another embodiment is a method of retrieving a synthetic neuromodulatory signal to be administered to a user. This method may be performed by a software or hardware process running in an electronic device, such as a portable electronic device. The process may include receiving a selection of a desired effect from a user interface of the electronic device. After the selection has been made by a user, the process may begin downloading a first synthetic neuromodulatory signal associated with the desired effect to the electronic device in response to the selection. The process may then receive an input of operational parameters from the user interface relating to application of the downloaded first synthetic neuromodulatory signal. It should be realized that this process may also be stored as instructions on a non-transient computer readable medium, wherein the medium contains instructions that when executed perform this process or method.

One additional embodiment is a neuromodulatory signal generator system that converts one or more measured peripheral nerve tissue signals to a neuromodulatory signal that may be applied to a user. This system may comprise a storage module having one or more measured peripheral nerve tissue signals taken from a subject subjected to a condition. The system may also have a processing module that communicates through a connection to the storage module so that the processing module may receive at least one of the measured peripheral nerve tissue signals. The processing module may be configured to process the at least one measured peripheral nerve tissue signal to form a processed measured peripheral nerve tissue signal. The neuromodulatory signal generator system may also have a state machine generator module communicating with the processing module to receive the at least one processed measured peripheral nerve tissue signal and configured to create a synthetic neuromodulatory signal. The synthetic neuromodulatory signal can be created by representing at least one of the processed measured peripheral nerve tissue signals as a sequence of one or more states. Each state may be represented by one or more state parameters that are converted to the synthetic neuromodulatory signal. The neuromodulatory signal generator system may also include a communication module that sends the synthetic neuromodulatory signal to a device configured to apply the synthetic neuromodulatory signal to the user, wherein application of the synthetic neuromodulatory signal to the user causes the user to experience a desired effect without application of the condition to the user.

One embodiment is also a method for converting one or more measured peripheral nerve tissue signals to a neuromodulatory signal that may be applied to a subject. This method may be a software or firmware process running in a neuromodulatory signal generator system. This method may include receiving at least one measured peripheral nerve tissue signal taken from a subject subjected to a condition. The process may then create a synthetic neuromodulatory signal by representing at least one of the measured peripheral nerve tissue signals as a sequence of one or more states wherein each state is represented by one or more state parameters that are converted to the synthetic neuromodulatory signal. Once the synthetic neuromodulatory signal is created, the process may send the synthetic neuromodulatory signal to a device configured to apply the synthetic neuromodulatory signal to a user, wherein application of the synthetic neuromodulatory signal to the user causes the user to experience a desired effect without application of the condition to the user. It should be realized that this process may also be stored as instructions on a non-transient computer readable medium, wherein the medium contains instructions that when executed perform this process or method.

An embodiment is also an electronic device for generating a neuromodulatory signal that may be applied to a user. The electronic device may be a wireless telephone or other electronic device. In this embodiment, the electronic device may include a user interface configured to receive a selection of at least one desired effect from the user. The device may also have a communication module that receives the selection from the user interface and connects to a remote neuromodulatory signal generation system to communicate the selection. Once the device has communicated the selection to the remote neuromodulatory signal generation system it may receive 1) a first representation of at least one neuromodulatory signal associated with the selection and 2) a set of parameters related to the selection. The parameters may be operational parameters in one embodiment. The device may also comprise a neuromodulatory signal generation module that receives the first representation of the at least one neuromodulatory signal and is configured to generate a second representation of the at least one neuromodulatory signal that is based on the first representation. The second representation may be in the proper format to be applied to the user, wherein application of the second representation of the neuromodulatory signal to the user causes the user to experience a desired effect without application of a drug to the user.

Yet another embodiment is a method or process for generating a representation of a neuromodulatory signal. This method or process may be carried out in an electronic device. In this embodiment, the process may include receiving a selection of at least one desired effect from a user. The process may then connect to a neuromodulatory signal generation system to communicate the selected effect and receive 1) a first representation of at least one neuromodulatory signal associated with the selection and 2) a set of operational parameters related to the selection. The process may then receive the first representation of the at least one neuromodulatory signal generate a second representation of the at least one neuromodulatory signal that is based on the first representation. The second representation may be applied to the user, wherein application of the second representation of the neuromodulatory signal to the user causes the user to experience a desired effect without application of a drug to the user. It should be realized that this process may also be stored as instructions on a non-transient computer readable medium, wherein the medium contains instructions that when executed perform this process or method.

Neurograms

Peripheral nerve neurograms or measured peripheral nerve tissue signals, such as vagus nerve neurograms, are primarily sensory signals that arise when a subject is placed under a condition. For example, the condition may arise from some stimulus or challenge presented to the subject. The neurogram can include highly structured spike trains, representing recruitment of many nerve fibers that appear to inform "caudal" (post-brainstem) targets about non-motor and mostly non-sensory somatic state.

Neurograms can be characterized in part by the evolution of firing rate and amplitude within the spike train. Different stimuli appear to give rise to distinct neurogram structures. For example, the neurogram response to visceral injection of tumor necrosis factor alpha (TNF-α) appears visibly distinct from a neurogram response corresponding to injection of interleukin one 1 beta (IL-1β) or insulin.

In one embodiment, neurograms were recorded from a peripheral nerve after placing a subject animal under the condition of being challenged with interleukin 1β. Using the recorded neurograms, a synthetic neuromodulatory signal that emulated the neurogram was created and administered to the animal. When the synthetic neuromodulatory signals emulating the neurogram were applied to peripheral nerve tissue of the animal, they were found to evoke responses associated with the particular interleukin 1β condition. For example, in response to application of the synthetic neuromodulatory signal emulating the IL-1β neurogram (3 repetitions, 12 minutes total), interleukin-6 appeared to be up-regulated in the animal, just as if IL-1β had actually been injected. In contrast, stimulation of peripheral nerve tissue with a synthetic neuromodulatory signal emulating an insulin neurogram was found to result in a marked rise in blood glucose in the animal some 40 minutes after the start of application of the signal (continuous loop, ~12 repetitions). Application of a synthetic neuromodulatory signal emulating an insulin neurogram may not mimic the complete effects of an insulin injection, however the synthetic neuromodulatory signal was able to cause a cascade of processes that ultimately resulted in release of glucose in the animal. This indicates that administering a neuromodulatory signal emulating a neurogram captured in response to a subject being under a particular condition can be useful to cause a biological reaction as if the animal was being subjected to the particular condition.

Neuromodulatory Signals

While neurogram recordings from a subject provide valuable raw material for neuromodulatory stimulation, relying solely on neurogram recordings to curate appropriate stimulus signals can be cumbersome. Instead, a neuromodulatory signal generator system can be used to generate synthetic neuromodulatory signals (NMSs) for nerve or tissue stimulation. The systems, methods, and devices disclosed herein can use the structures of different neurograms to build parameterized state-machine models of synthetic neuromodulatory signals to evoke particular, specific responses in an animal or human. The synthetic neuromodulatory signals can be modified by changing the state parameters which were used to create the synthetic neuromodulatory signal. The neuromodulatory signal generator system may optimize the synthetic neuromodulatory signals by modification of state parameters. The state-machine models can be stochastic or deterministic. NMS state parameters may include spike waveform properties, firing rates and amplitudes.

In one embodiment, the method uses a sequence of states and transitions to define the characteristics of the NMS to be generated to the individual. The "atomic" unit of the NMS can be a waveform template that may have the same shape and features as a neuronal spike. This template can include parameters including signal width, depolarization amplitude, and after hyperpolarization (AHP) amplitude.

Each state in the state-machine model can define a set of parameters that can be used to stochastically, or deterministically, generate neuromodulatory signals (NMSs) in the form of a spike train of desired amplitude and rate. In one embodiment, each state represents a probability distribution over spike amplitudes, firing rates, and may also include waveform characteristics, as well as state duration. The probability distributions can be parameterized. For example, a log-normal distribution over amplitudes will include a mean and a standard deviation. For deterministic patterns, the latter can be set to zero. A Poisson distribution can be defined for establishing firing times, or a constant firing rate can be used. These probabilistic models can be used to generate a statistically stationary spike train of specified duration that is produced by that state. A transition between states can be defined by a duration, and implemented by linearly blending the generator functions (probability distributions) from one state to the next. Instead of linear blending, a cubic spline may be used to ensure smoothness. The transition duration controls the speed with which the amplitude and firing rates change from state to state, and allow us to control the envelope of the stimulus packet. In one embodiment, a state can be based on modulation by periodic change in amplitude or rate, linear progressions in amplitude or rate, zero-time transitions, and/or compression.

In one embodiment, a NMS can be defined by a sequence of states that identify distribution parameters and duration for spike train generation at each state, along with state transitions that define duration and state-to-state interpolation methods. New neuromodulatory signals can be generated at will without the need for surgery, recording, or sacrifice of animal subjects.

FIG. 1 is a data flow diagram that shows that a "state" $S_n$ of an electrical signal can be represented by three or more properties: (1) a waveform, represented as a sum of time delayed functions, (2) an amplitude distribution (a gain, or scale factor applied to the waveform shape) with mean and variance, and (3) a mean firing rate with variance. In alternative embodiments, there can be any number of properties. Each function can be parameterized by a mean and variance in time. Each function can be a Gaussian function, a quadratic function, or a higher order function. This representation is used to generate spike-like signals that use a specified waveform, scaled by the desired amplitude parameters, and exhibiting the desired mean firing rate. Each state is a stochastic model for a spike train. When variances are set to zero, the model becomes deterministic. Each state can be represented by one or more state parameters that are used to generate a synthetic neuromodulatory signal for a particular effect on an animal or a human patient.

Figure 2:
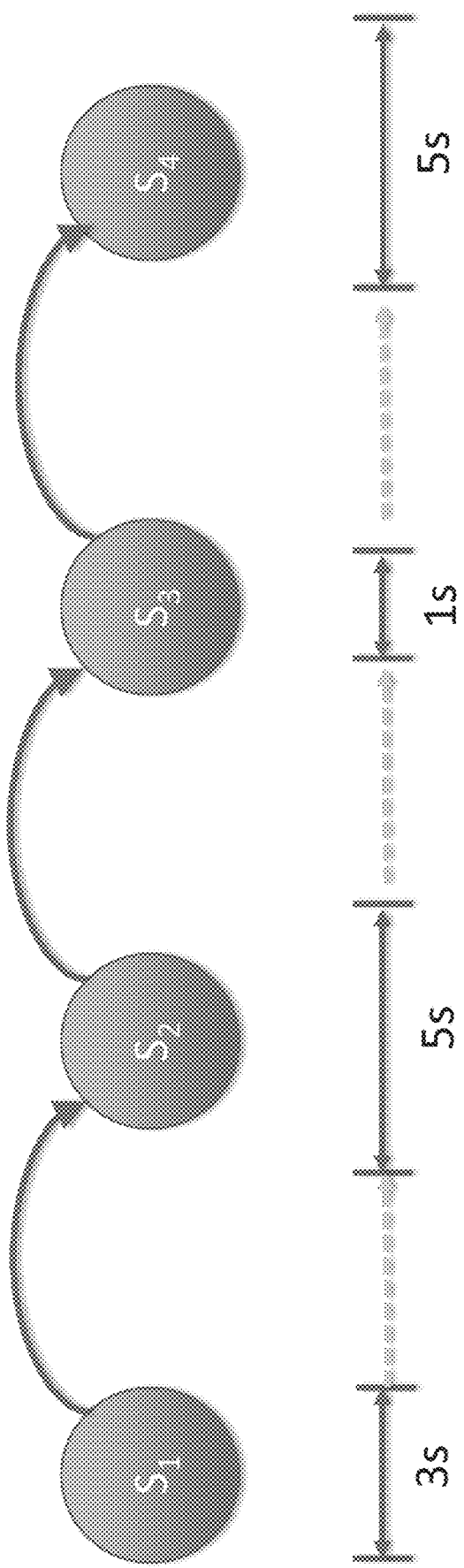
FIG. 2 is a schematic illustration showing that states with different durations can be separated by transitions.

FIG. 2 is a diagram showing that states with different durations can be separated by transitions. A stimulus can be represented as a sequence of states, each with stationary statistical properties: waveform parameters, amplitude mean and variance, firing rate mean and variance. Each state can have a fixed duration specified in a time unit, such as seconds. Each transition between two states can also have a fixed duration. A state, such as the state $S_n$, can be one of a number of states with different durations and having transitions separating the different states. State transitions can be implemented as an interpolation of one or more state parameters from one state to the next. For example, waveform parameters, amplitude distribution parameters, and firing rate parameters can be independently interpolated using a polynomial fit from one state to the next. One example system can implement linear interpolation or cubic spline interpolation.

In one embodiment, a state model is learned directly from data of recorded spike trains from a neurogram. For example, the recorded signal from a vagus nerve can be "compiled" into a compact state-machine representation for subsequent signal synthesis. The data of recorded spike trains can be sorted into a sequence of time stamped spikes. A sorted spike sequence can be compiled into time intervals containing constant mean amplitudes and firing rates using binning in time. The bin size can be determined automatically or chosen by the user. Each such interval can be declared to be a state. Means and variances can be computed for amplitude and firing rate values. Waveforms within the interval can be averaged and a 2-Gaussian mixture can be fitted to this average waveform using a standard numerical optimization scheme over the Gaussian parameters. Each state can thus be defined with its durations determined by the time intervals where the state has been inferred. Parameters of the state model can be referred to as neuromodulatory signal parameters of the model. State transition durations can be determined by using the gaps between successive intervals.

The shape of a recorded neurogram may represent an "address," informing nerve afferents about the nature and anatomical source of the signal. For example, the shape of a nerve signal can represent sources in the central nervous system from the periphery through the brainstem, informing vagus nerve afferents about the nature and anatomical source of the signal. In one embodiment, this signal structure may be used as a type of anatomical addressing scheme that a nerve, such as the vagus nerve, uses to communicate the nature and location of peripheral disturbances to central homeostasis regulators within the body.

In some embodiments, the combination of biochemical stimulus (e.g. cytokine mixture), anatomical location (spleen, vs. liver), and distance (axon length) can give rise to different signal structures under different circumstances. Even for a given biochemical or physical stimulus, propagation delays induced by axon length may give rise to different neurogram structures depending on the location of the stimulus.

One embodiment of the invention is a stimulus signal synthesis framework that views the stimulation problem in terms of programming a state machine—an abstract formalization of the peripheral nerve-to-CNS system, such as vagus-to-CNS system. Each state and transition in the state machine may include parameters that define duration, waveform properties (including those likely to differentially affect A, B, and C fibers of a nerve, or any other neuron-dependent electrical properties), and spike timing. This state-machine model is general enough to synthesize the space of possible peripheral nerve-to-CNS signals, such as vagus-to-CNS signals. With this combined framework in place, the synthetic neuromodulatory signal from a state-machine representation can be optimized for stimulating a peripheral nerve or tissue with specific spike train signals to enhance performance of each CNS subsystem of interest in the body. In one implementation, that stimulation can be electrically applied to the nerve directly, or transduced through mechanical (e.g., sound), optical (i.e., light), or other means by modulating the supplied energy using the stimulus patterns generated by our approach. This allows a programmatical approach to stimulating nerves to result in a desired physiological outcome within the target individual.

Modeling the Neurogram

Figure 3A:
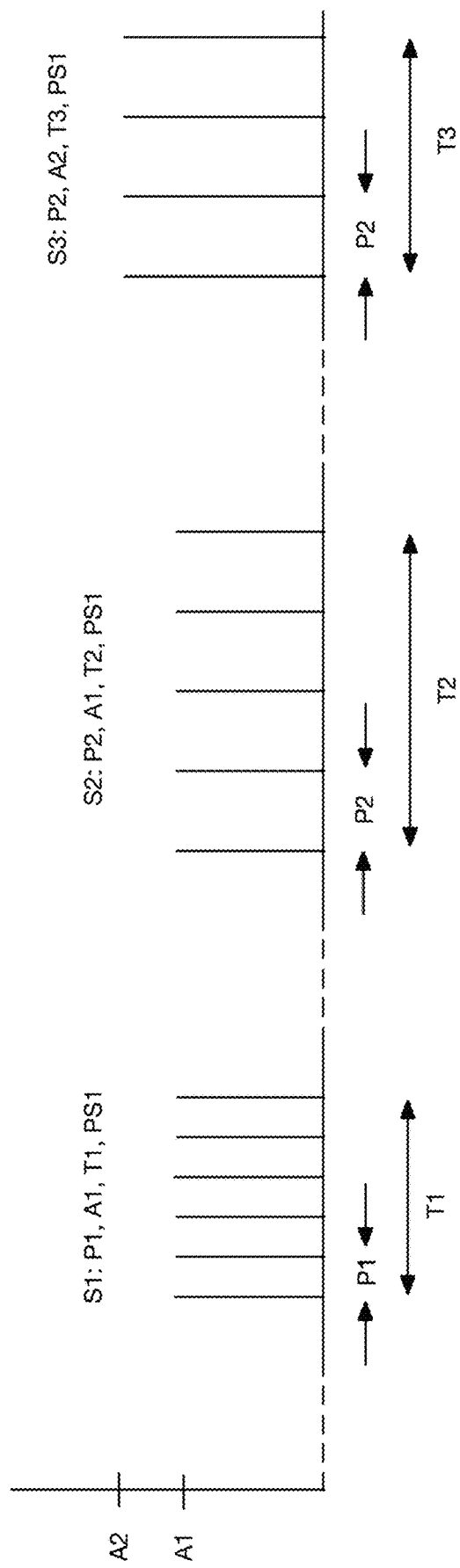
FIG. 3A illustrates a sequence of three states where each state is characterized by a set of parameters.
Figure 3B:
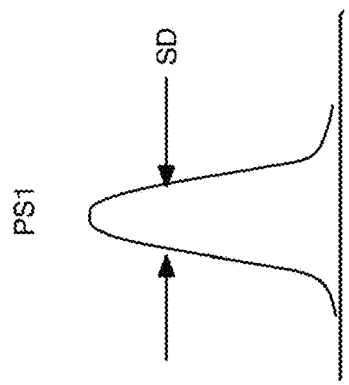
FIG. 3B shows an example base pulse shape.

In one embodiment, the neurogram is modeled as a sequence of one or multiple states where each state corresponds to a time period or segment within the recorded neurogram that has statistically stationary properties. Each state may be represented by one or more state parameters, such as the duration of the state, the inter-pulse timing (inverse of the firing rate) of the pulses, the amplitude of the pulses, the mean and variance of the inter-pulse timing, the mean and variance of the amplitude, the base pulse shape. FIG. 3A illustrates a sequence of three states where each state is characterized by a set of state parameters. In this example, the states are characterized by four state parameters: inter-pulse timing (P), amplitude (A), duration (T) and base pulse shape (PS). These four state parameters may be termed "waveform parameters" as they describe characteristics of the waveform. The three states are denoted by S1, S2 and S3. Thus, S1 is characterized by inter-pulse timing P1, amplitude A1, duration T1 and base pulse shape PS1. The base pulse shape is described further with reference to FIG. 3B. Each of the spikes seen in FIG. 3A, when observed in a magnified scale, may have a shape and/or a finite width. An example of a base shape is illustrated in FIG. 3B. The base shape may thus be characterized by a function, such as a Gaussian. Each shape may further be characterized by one or multiple state parameters. In this example, since the base shape is a Gaussian, the shape may be characterized by the standard deviation SD. Thus, the state parameter that describes the base pulse shape within the set of state parameters that describe the state may specify the specific shape and any associated state parameter that defines the width or other characteristics of the shape. In some embodiments, these state parameters may be used to generate synthetic neuromodulatory signals within the body.

FIGS. 3A-3B do not show any statistical variation of the state parameters although it is possible that one or more of these state parameters may have some statistical distribution in real-life circumstances. The statistical variation of each state parameter may itself be parameterized and included in the set of state parameters that represent each state. The variation can be modeled after observations of the recorded neurograms. For example, the variation in the state parameters may be modeled by a Gaussian distribution or a log-normal distribution. Further, the state parameters may vary differently from each other. As an example, the inter-pulse timing may vary according to a Gaussian distribution whereas the amplitude may vary according to a log-normal distribution.

Accordingly, a neurogram can be modeled as a sequence of states where each state is represented by a set of state parameters. Some of these state parameters describe the waveform and some others describe the variability of their values. While a state-space representation is used to model a neurogram, it may be possible to use other techniques as well. The phrase "signal representation" is used to depict any technique that is used to represent a neurogram including the state-space representation.

Parallel Synthesis

Figure 4:
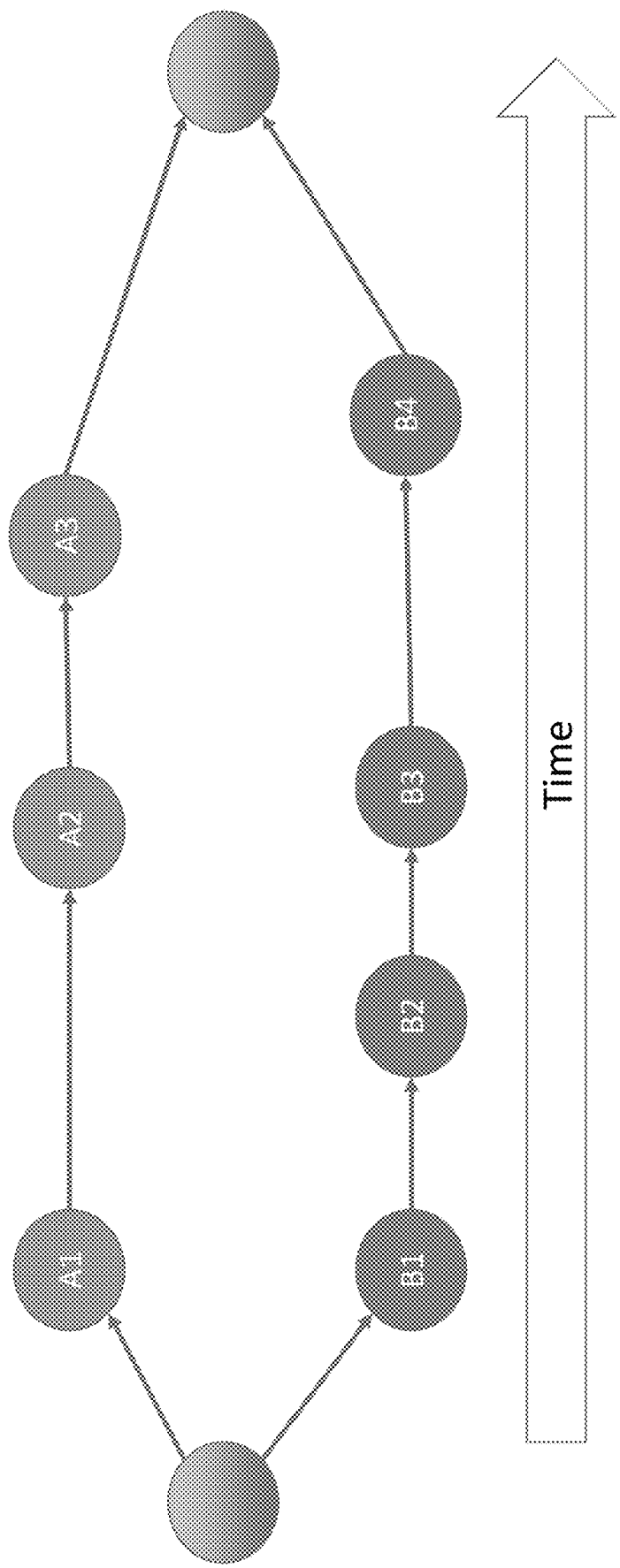
FIG. 4 is a schematic illustration of a state machine with multiple threads.

In one embodiment, a neurogram can be a result of cells or groups of cells exhibiting distinct behaviors. Such neurogram can be modeled using a state machine with multiple threads. FIG. 4 shows a state machine with two threads, thread A and thread B. Thread A includes three substates, A1, A2, and A3. The substates A1, A2, and A3 may be a result of a first group of cells exhibiting a first type of behavior. Thread B includes four substates, B1, B2, B3, and B4. The substates B1, B2, B3, and B4 may be a result of a second group of cells exhibiting a second type of behavior. Each thread can include state parameters for generating a partial synthetic neuromodulatory signal. For example, each of the substates A1, A2, and A3 can be associated or modeled using state parameters such as a waveform, amplitude distribution, and a mean firing rate. Thread A can generate a partial NMS based on the state parameters of the substates A1, A2, and A3. For example, thread A can generate a partial NMS using the state parameters of the substate A1, a partial NMS using the state parameters of the substate A2, and a partial NMS using the state parameters of the sub state A3. These three partial neuromodulatory signals can be combined, with time delay, to generate a partial NMS. Thread B can generate a partial NMS based on the parameters of the substates B1, B2, B3, and B4. For example, thread B can generate a partial NMS using the state parameters of the substate B1, a partial NMS using the state parameters of the substate B2, a partial NMS using the state parameters of the substate B3, and a partial NMS using the state parameters of the substate B4. These four partial NMS can be combined, with time delay, to generate a partial NMS.

The partial NMS generated by each thread can be combined to generate the full neuromodulatory signal. For example, signals generated by each thread can be first time delayed, and then summed or superposed to generate the full neuromodulatory signal. The systems, methods, and devices disclosed herein can be implemented as a multi-threaded state machine for processing a neurogram that results from cells or groups of cells exhibiting distinct behaviors.

Recording, Processing, and Applying Signals

Figure 5:
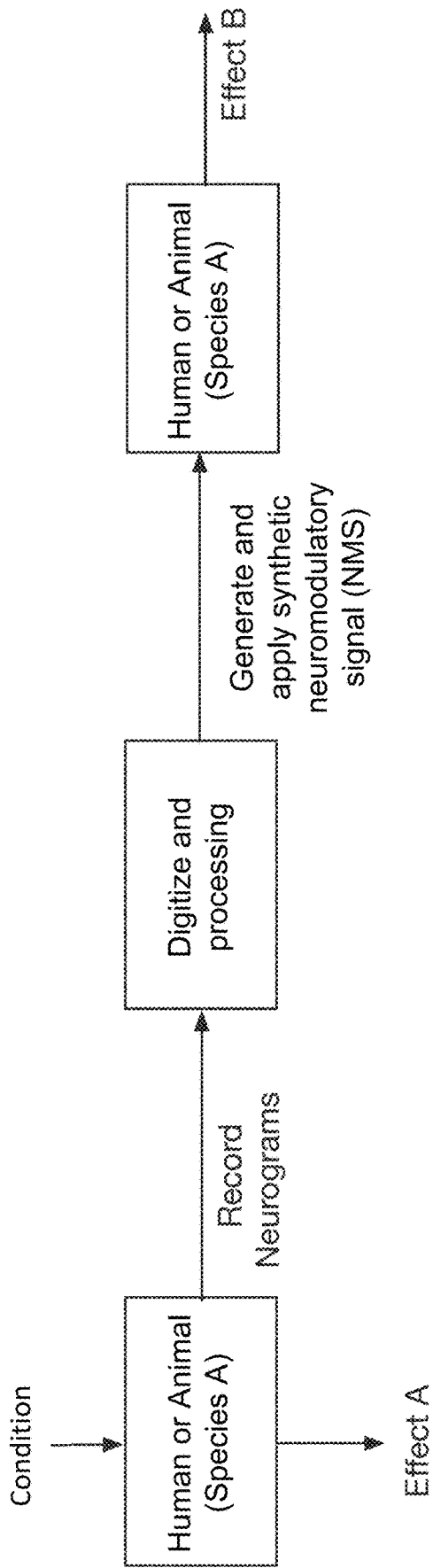
FIG. 5 illustrates a method to process neurograms using a state machine model to generate synthetic neuromodulatory signals (NMS) and applying a representation of an NMS based on certain NMS parameters.

FIG. 5 illustrates a method to record and process neurograms using a state machine model to generate and apply synthetic neuromodulatory signals. In this figure, a stimulus is applied to a human or an animal 1 of a species A to elicit a desired effect (effect A). The resulting neurogram(s) are recorded during the process of applying the stimulus. The recorded neurograms can be digitized and processed using a state machine to generate state-machine representations of the neurograms. Processing can include, for example, filtering, amplifying, interpolating, analyzing, decomposing into spectral components, clustering, modifying, synthesizing, and/or other signal processing techniques. Processing can include converting the neurogram to a finite state machine representation of the neurogram. A state-machine representation can include one or more state parameters, which can be used to generate synthetic neuromodulatory signals to the same or different human or animal of the same species. The processed neurogram and resultant synthetic neuromodulatory signal can be constructed to elicit the same or similar effect on the same or different animal as the effect A (which resulted from application of the stimulus to the first animal). For example, when a cytokine (a small protein that plays a role in cell signaling) TNF-alpha is injected into an animal, a pro-inflammatory response is generated. Generally, after such an injection, a fever quickly ensues and subsides. But about 4 hours later, there is a second wave of fever, possibly brought on by an increase in IL-1 (interleukin-1, another cytokine that plays a role in regulation of immune and inflammatory responses to infections) that is triggered by TNF-alpha. The disclosed systems, devices, and methods can be used to fight infections or other conditions by provoking the body's response to TNF-alpha without the need for a physical injection of the cytokine. For example, once the stimulus, transition, and response characteristics are known, the system can generate a synthetic neuromodulatory signal, which, when applied e.g. via electrical stimulation of the nervous system, is designed to signal to the brain that TNF-alpha is present in the blood stream (without actually injecting TNF-alpha).

Figure 6:
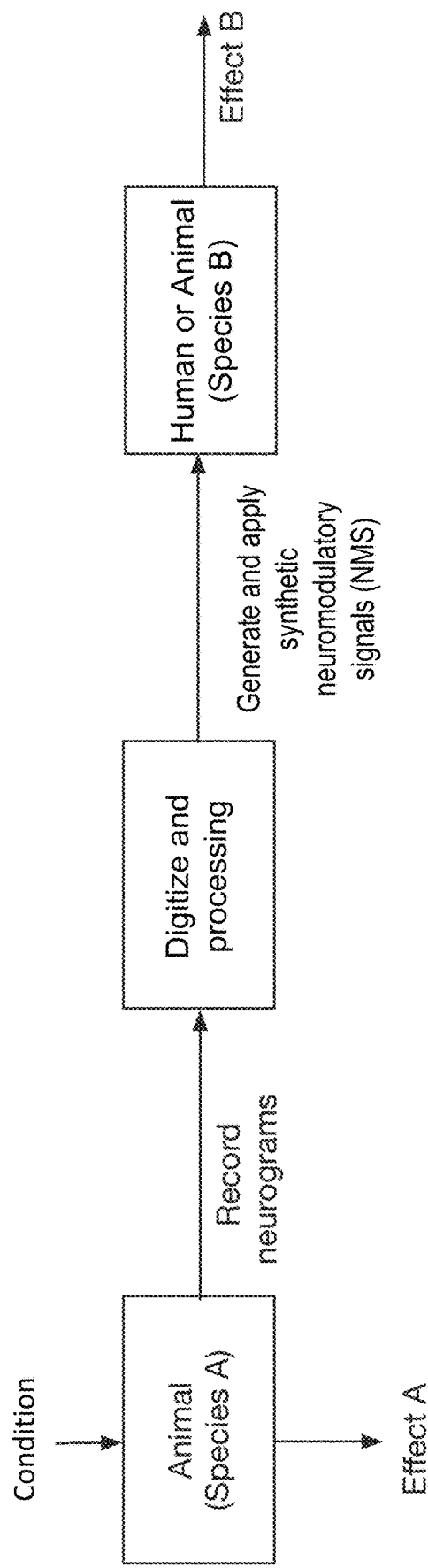
FIG. 6 illustrates another method to process and apply neurograms using a state machine model to generate synthetic neuromodulatory signals and applying a NMS representation based on certain NMS parameters.

FIG. 6 illustrates another method to record and process neurograms using a state machine model to generate and apply synthetic neuromodulatory signals. In the method of FIG. 6, a neurogram is generated as a result of applying a condition to one species of an animal. That neurogram is used to generate a synthetic neuromodulatory signal that is processed and applied to a human or an animal of a different species. Thus, in this embodiment, a condition is applied to one or more animals of one species (species A), and the resulting neurograms are recorded, processed and the resultant synthetic neuromodulatory signals are applied to one or more humans or animals of a different species (species B).

Alternatively, or in addition, processing the neurogram into the synthetic neuromodulatory signal may include additional modifications of the synthetic neuromodulatory signal to accommodate differences in anatomy and physiology and/or other characteristic differences between animals of species A and humans or animals of species B. As an example, while neuromodulatory signals with a specific amplitude may elicit a certain response in animals of one species, NMSs with a different amplitude may be appropriate for eliciting the same response in animals of a different species. As another example, a NMS of a certain time duration may elicit a specific response in an animal of one species, while a NMS of a different time duration may be appropriate for eliciting the same response in a human or an animal of a different species. Other examples of the NMS state parameters that can be modified include the frequency of the underlying component or components of the recorded neurogram and state parameters used to accommodate the stimulating device. In general, the NMS state parameters resulting in an expected response, or other characteristics of a neurogram, may vary across different species or even within the same species.

Figure 7A:
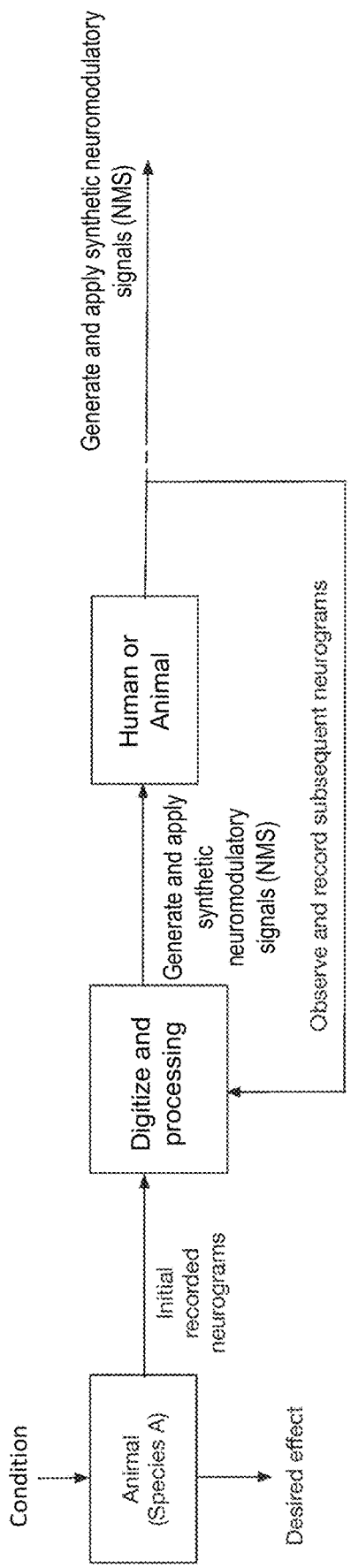
FIG. 7A is a flow diagram of iterative processing of recorded neurograms.

FIG. 7A illustrates iterative processing of recorded neurograms. In this processing technique, an initial neurogram is recorded based on application of a condition to an animal of species A, resulting in a desired effect in the species A animal. The initial recorded neurogram is then processed to form an initial synthetic neuromodulatory signal as discussed above. The initial synthetic neuromodulatory signal is then applied to a second human or another animal of the same or different species as the first animal to produce a subsequent neurogram. The effect of administering the initial synthetic neuromodulatory signal is measured by comparing the initial neurogram to the subsequent neurogram. With this technique, the subsequent neurograms may be processed into additional synthetic neuromodulatory signals and administered back into the animal or human multiple times using a feed-back loop and in an iterative manner, where further modifications of the synthetic neuromodulatory signal may be determined on the basis of the observed effect after each iteration. The iterations may continue until the observed effect converges to an acceptable level of consistency such that the synthetic neuromodulatory signal is inducing the animal or human to emulate being under the original condition. Use of this technique can help establish the efficacy and safety of applying synthetic neuromodulatory signals that emulate the neurograms.

Figure 7B:
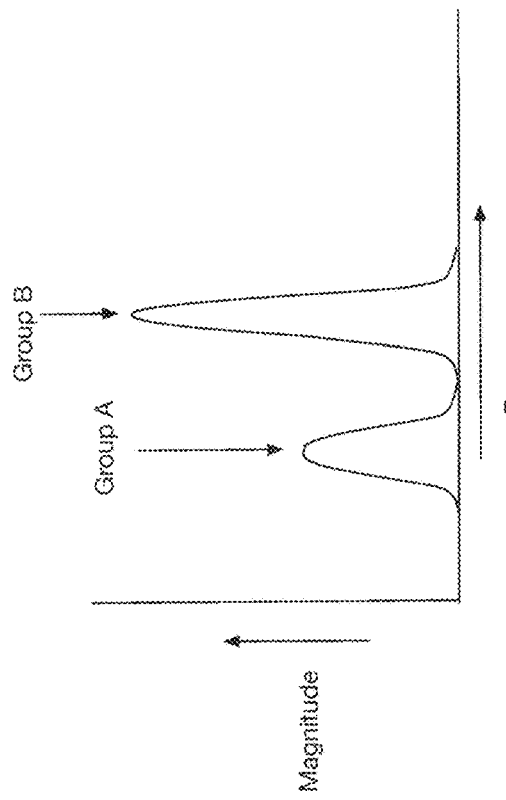
FIG. 7B is a depiction of an embodiment of a processed neurogram.

An example of a NMS is illustrated in FIG. 7B. In this example, an initial recorded neurogram is decomposed into multiple components and the effect on an animal (of the same or different species) or a human of some or all the components, individually or in combination, is observed and characterized. Further, the neurograms of the animals receiving the components of the NMS generated using synthetic neuromodulatory signals derived from the initial recorded neurogram can be recorded and used to further iterate the synthetic neuromodulatory signals using the iterative loop described in FIG. 7A. In one example shown in FIG. 7B, an initial recorded neurogram is decomposed into its spectral components, which can be modeled using NMS state parameters. As shown in FIG. 7B, the spectrum may have a bimodal shape in which the signals contained within a group A include lower frequency components and the signals contained within group B contain higher frequency components. The NMS state parameters of the two components can be filtered and the filtered NMS state parameters can be used to generate a synthetic neuromodulatory signals for application to other animals or humans. Thus, NMS generated using NMS state parameters derived from each component group can be applied by themselves and the effect on the animals or humans may be observed. Further the neurograms may be recorded while the filtered components are applied; these recordings may be used to iterate synthetic neuromodulatory signals such that a desired effect on animals or humans is achieved.

An Applications Library for Synthetic Neuromodulatory Signal Submission

FIG. 8A illustrates a system diagram in which a library or repository of synthetic neuromodulatory signals may be stored in computer memory. For example, the library can be stored on a network-accessible system or "the cloud". Synthetic neuromodulatory signals can be submitted to the applications library for storage and use in various applications or for use by one or more specific end users or end user populations. The library can be part of a remote neuromodulatory signal generator system. For example, a set of synthetic neuromodulatory signals in the library may be associated with a specific desired effect (e.g. 1 to N). A user may download a set of synthetic neuromodulatory signals to a local computing device, such as an electronic device, and apply it to himself or herself, or to others, in order to experience the desired effect. As an example, a user may desire to suppress his or her appetite. A user may have a prescription for a specific desired effect that can be generated using a set of synthetic neuromodulatory signals. The local electronic device can download the set of synthetic neuromodulatory signals based on the prescription. A set of synthetic neuromodulatory signals for suppressing appetite may exist within the library as a result of prior submission of the set of synthetic neuromodulatory signals to the library either by the user or another entity. The appetite suppression synthetic neuromodulatory signals may be downloaded by a user and applied to the user or another subject, using a local neuromodulatory generator system. The library may be accessed through any suitable network or communications link, including wireless, optical or wired computing systems. In some embodiments, a set of synthetic neuromodulatory signals can be stored as a neuromodulatory signal program, which contains the synthetic neuromodulatory signals that describe the one or multiple states along with control data that contains information about how the stored neuromodulatory signals may be used.

The applications library can be configured in many different ways. In one embodiment, different types of users may be allowed different levels of access. Access control mechanisms may be employed to restrict access to only those synthetic neuromodulatory signals that have been approved for use by the user. As an example, the general public may be allowed to only access certain types of synthetic neuromodulatory signals that are tested and safe to be applied to humans. On the other hand, researchers may be permitted to access certain other types of synthetic neuromodulatory signals that may be inappropriate to apply to humans but may be applied to non-human animals. In one embodiment, doctors or other health care professionals may "prescribe" NMSs or certain effects, such that only human patients with valid prescriptions may be allowed access to such NMS s.

For a class of NMSs that provide therapeutic or other health benefits, the disclosed system enables testing of the safety and/or efficacy of each NMS, before the synthetic neuromodulatory signal is permitted to be downloaded from the library. In some embodiments, tests in animals are performed for safety and efficacy and neuromodulatory signals that pass these safety tests are indicated as such within the library (e.g. by appropriate labeling). Alternatively, or in addition, synthetic neuromodulatory signals may be tested using clinical trials in humans. After such testing, if the desired effect is achieved, the synthetic neuromodulatory signals can be stored within the library along with the appropriate labeling. Once stored in the library, users may download these types of synthetic neuromodulatory signals with the knowledge that the indicated testing has occurred.

Another method to test for safety of a synthetic neuromodulatory signals is illustrated in FIG. 8B. A set of state parameters, which can be a state machine representation of a NMS, can be used to generate a synthetic neuromodulatory signal known to be safe. The set of state parameters for generating a safe synthetic neuromodulatory signals may have been generated on the basis of prior knowledge such as through experimentation on a test group of animals. When an untested NMS is to be checked for its safety characteristics, the set of NMS state parameters, which can be a state machine representation for generating the untested NMS can be tested. The two sets of NMS state parameters, or state machine representations, are compared. Based on the comparison of the state machine representations of the tested and untested NMSs, a determination can be made as to whether the untested NMS can be applied to a human or another animal subject. If the comparison is successful, then the set of NMS state parameters for generating the newly tested NMS may be uploaded to the library.

Figure 9:
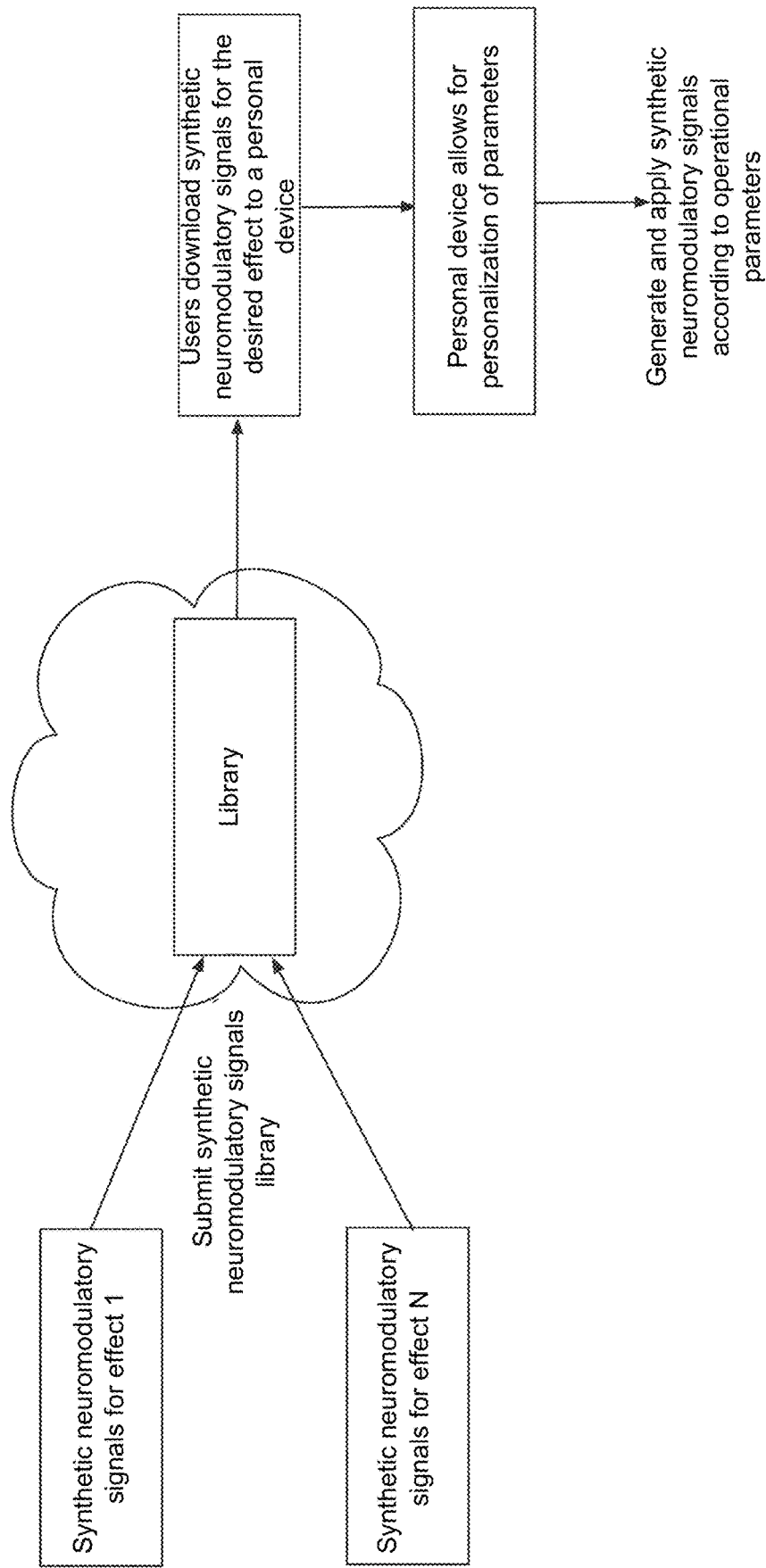
FIG. 9 is a schematic diagram of another synthetic neuromodulatory signals library for personalizing a NMS for application to an animal or human user.

FIG. 9 is a schematic diagram of another library for personalizing an application of a synthetic neuromodulatory signals to an animal or a human. As illustrated in FIG. 9, system users or the system itself can personalize the effect that is desired to result from application of a synthetic neuromodulatory signal. As an example, if a synthetic neuromodulatory signal is designed to manage pain, then if a user has mild pain, he or she may select a operational parameter that applies the synthetic neuromodulatory signal. In addition, the system may also detect the need to apply operational parameters to properly apply the synthetic neuromodulatory signal to the animal or human. If a user is experiencing a greater level of pain, the end user may select a operational parameter that applies the same synthetic neuromodulatory signal for greater amounts of time up to a certain maximum limit (which may be determined through safety testing). In the illustrated system, personalization is enabled when a synthetic neuromodulatory signal is downloaded to a personal electronic device. Some aspects of a NMS that can be personalized by the system include the context specific operational parameters such as dates, calendars, exercise, or time of day. Other operational parameters may allow changes to the amplitude control of the nerve stimulation to account for differences in transfer function from stimulator to the nerve. Some modifiable operational parameters may include the length of application time, the duration time for application of the synthetic neuromodulatory signal, and the frequency of application of the synthetic neuromodulatory signals.

Figure 10:
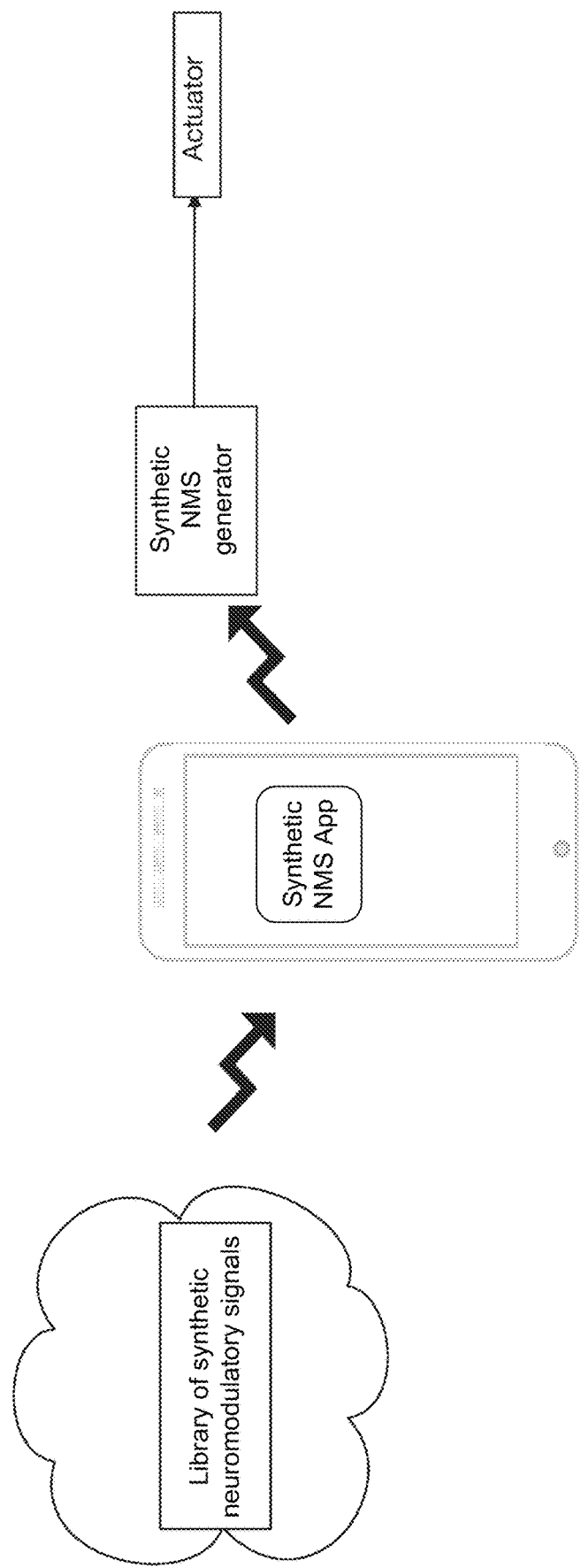
FIG. 10 is a schematic diagram of a system that allows downloading of a set of synthetic neuromodulatory signals for generating a representation of one or more NMS and applying the specific representation of the NMS generated.

FIG. 10 is schematic diagram of a system that allows selection and downloading of a synthetic neuromodulatory signal from cloud storage repository to a local device (e.g. a smartphone, tablet computer, or smart wearable device) and applying a specific synthetic neuromodulatory signal to a subject. An end user may initially download a "neurogram app" software application or other widget to his or her smart phone or other electronic or mobile device. Through the neurogram app, a user can connect to the cloud storage and select a synthetic neuromodulatory signal that provides a desired effect. A file containing the synthetic neuromodulatory signal is then download to his or her device. A user can have one or several such synthetic neuromodulatory signals downloaded and stored in his or her electronic device at any particular time. Then, the user can choose the appropriate synthetic neuromodulatory signal to administer to achieve a desired effect at a particular time. The device may then transmit the selected synthetic neuromodulatory signals to a NMS generator, which can modify the synthetic neuromodulatory signal according to certain operational parameters for the particular applicator being utilized to apply the synthetic neuromodulatory signal to the subject. The subject may be the end user or another human or animal subject, for example.

In the context of the application of synthetic neuromodulatory signals, an applicator can be a device that applies the synthetic neuromodulatory signals to human or non-human animals or to other equipment, such as test equipment. In some configurations, the signals that drive the applicator may be generated by the device itself. For example, the end user's electronic device may be equipped with hardware and/or software functionality for controlling the applicator. Various types of applicators may be utilized including but not be limited to speakers, headphones, ear buds, electrodes, light emitting diodes or other light-emitting devices, mechanical vibrators, RF transducers, electromagnetic, other mechanical or electromechanical devices.

In one embodiment, an example system provides user identification, which can be used to prevent unauthorized use. Different levels of security can be utilized for different end users or subject populations. As an example, the native capabilities of the smart phone to verify the identity of the end user may be used to verify that a synthetic neuromodulatory signal is approved for use by the end user. Authentication methods may include passwords, iris, retina, fingerprint, camera or other methodologies or combinations. If the user is verified, the user device can output the selected synthetic neuromodulatory signal for application to the subject by an applicator. As another example, user specific biometric data, such as the user's finger print, can be sent to an institution maintaining the applications library first. The institution can include this biometric information as part of the application that is downloaded by the user. When the user tries to apply this synthetic neuromodulatory signal, the end user's device asks the user to supply a sample of the biometric (fingerprint in this example) and compare the supplied biometric sample to the biometric data that has been downloaded as part of the application. If the biometric sample matches the reference biometric, a match is obtained, and the end user's device outputs the synthetic neuromodulatory signals for application to the subject by an applicator. Thus, these and other techniques can be utilized to prevent unauthorized use of synthetic neuromodulatory signals.

A full system enabling the restoration of health and mitigation of disease through tissue or peripheral nerve stimulation, such as vagal stimulation, can include other layers of functionality. For example, the disclosed system can include a middleware layer. Such middleware may provide an interface by which specific functions of the device's operating system may communicate with device drivers at a lower level and with higher level applications. By providing a middleware layer, higher level applications are able to achieve functions independently of specific details of the lower level implementation.

Synthetic Neuromodulatory Signal Generator System

Figure 11:
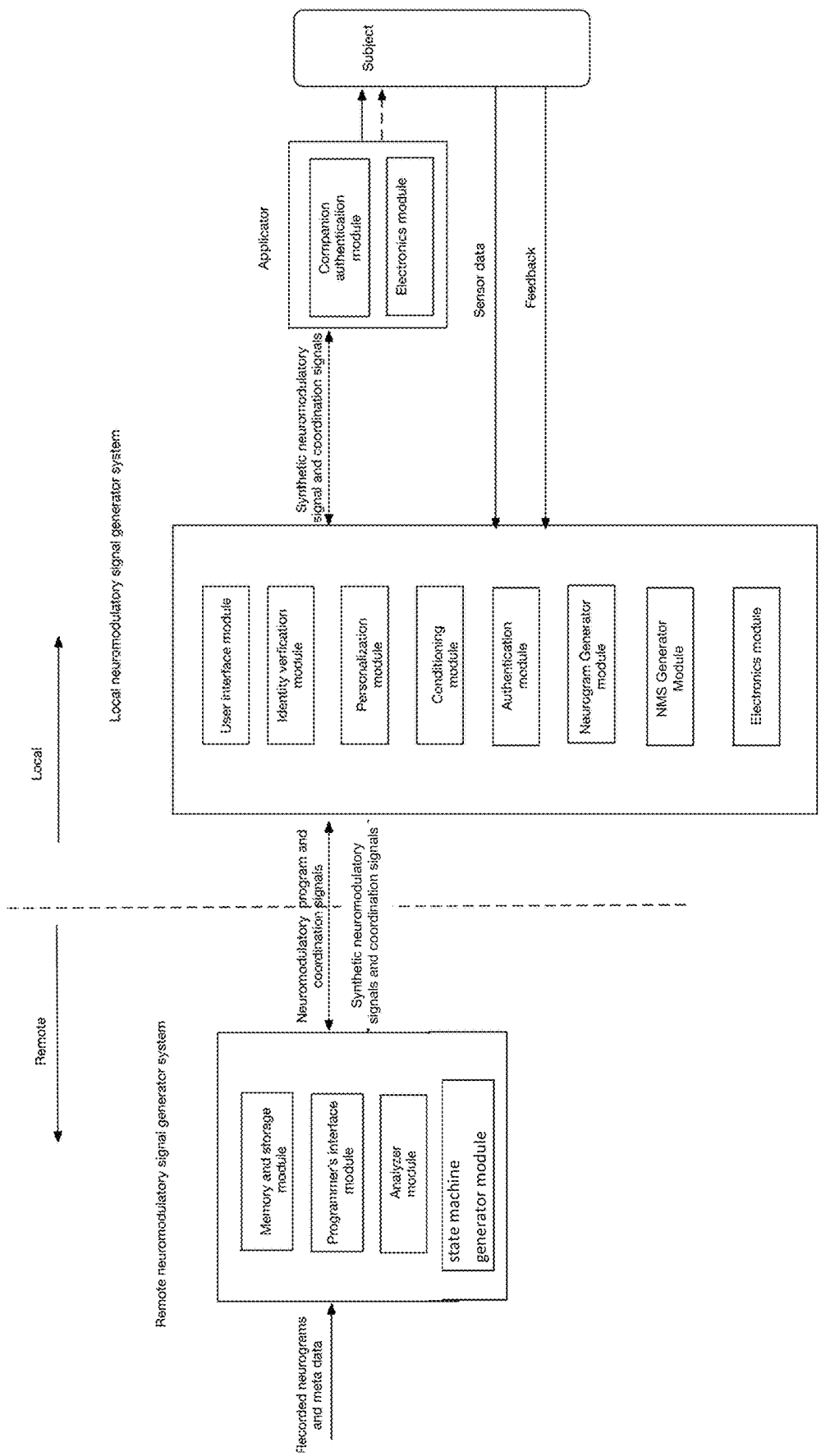
FIG. 11 illustrates a functional block diagram of neuromodulatory signal generator system.

FIG. 11 illustrates a functional block diagram of synthetic neuromodulatory signal generator system. This system can generate synthetic neuromodulatory signals that may be applied to a subject to elicit desired effects, such as to control of glucose levels, appetite suppression etc. The subjects can be humans or animals. This system can be configured in multiple ways and one configuration is illustrated in FIG. 11. In this configuration, there is a remote neuromodulatory signal generator system and a local neuromodulatory signal generator system. Each system can consist of one or multiple modules, each module responsible for generally achieving one or multiple functions. Some modules can be located remotely while some others may be located locally (in relation to the subject). With the understanding that other configurations are possible, the modules that can be located remotely include a memory and storage module, programmer's interface module, an analyzer module and a generator module. The modules that can be located locally include a user interface module, a neuromodulatory signal generator module, a personalization module, a conditioning module and an electronics module. The local neuromodulatory signal generator system can thus produce synthetic neuromodulatory signals that may then be applied to a subject.

Remote Functions

As seen in FIG. 11, some modules of the synthetic neuromodulatory signal generator system are set up remotely within a remote neuromodulatory signal generator system (also called the "remote system" in this disclosure). The benefit of such a configuration is that it allows experimentation, analysis and testing of neuromodulatory signals prior to dissemination and use on subjects. Another benefit of such a configuration is that the compute intensive resources do not need to be located on the local generator system, enabling the local generator system to have advantageous characteristics, such as being compact, inexpensive and perhaps entirely encapsulated as an application on a smartphone.

In one embodiment, one or several sets of synthetic neuromodulatory signals can be input into the remote neuromodulatory signal generator system along with the metadata about the synthetic neuromodulatory signals to be generated that the metadata can provide information about the conditions under which the synthetic neuromodulatory signals are obtained. These sets of synthetic neuromodulatory signals may be obtained from neurograms recorded during the performance of experiments on animals in laboratories. For example, neurograms can be obtained by placing electrodes on the peripheral nerve, such as vagus nerve, of mice and recording and digitizing the signals after a specific stimulus has been delivered to the animal. In one embodiment, these neurograms are processed into specific data that may be transmitted to a local neuromodulatory signal generator.

Remote Neuromodulatory Signal Generator System

Figure 12:
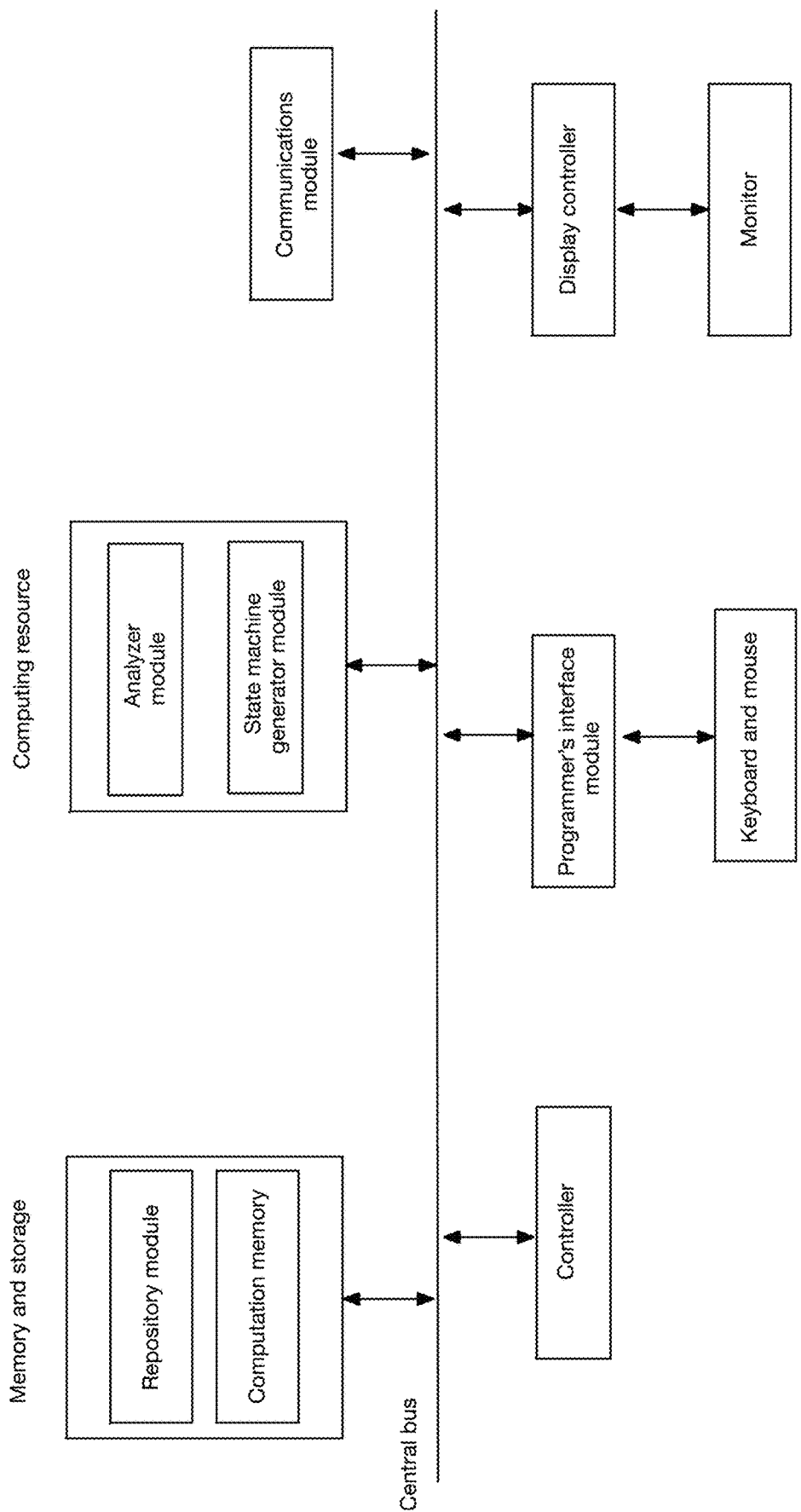
FIG. 12 is a functional block diagram showing an example remote neuromodulatory signal generator system.

The modules of the remote neuromodulatory signal generator system can be configured in several ways. One configuration is illustrated in FIG. 12. In this configuration, a central bus connects the various resources, such as the memory and storage module, a controller, a computing resource, a programmer's interface module and a communications module. The computing resource can be centralized or can be distributed and may be implemented with one or a combination of central processing units (CPU), field programmable gate arrays (FPGAs) and graphical processing units (GPUs). The controller can be another computing resource that coordinates and controls the overall activity of the remote neuromodulatory signal generator system. The memory and storage module can be centrally localized as illustrated in the figure or can be distributed across several physical entities, such as read-only memory, random access memory, flash etc., within the system. Along with the various functions that memory and storage normally provides within a computing system, this module serves as a repository for the neurograms along with the metadata of each neurogram. This module can also provide memory for the computation resources to store the intermediate or final results of computations. Next, the communications module allows the system to communicate to external computing resources or devices using one or several mechanisms, such as Bluetooth, Wi-Fi, Ethernet. etc.

The remote neuromodulatory signal generator system may also be capable of performing a computation of a quality factor. This quality factor may represent how closely the state machine representation, when converted back to a synthetic neuromodulatory signal, matches one or more of the input neurograms. The match may also be made between the converted synthetic neuromodulatory signal and a representation of the one or more input signals. The representation may be obtained by averaging time corrected and amplitude normalized neurograms. The match may be found using various techniques such as correlation techniques or regression techniques. When a quality factor is computed, a subsequent action may be taken by the remote system. One example of a further action is that depending on a value of the quality factor, and depending on a comparison value set by a user of the remote system, the state parameters may be either sent or not sent to the local system if the value has not reached a threshold. Another action is that the quality factor may be used in an automatic or manual feedback loop where the state representations are iterated until an appropriate quality factor threshold value is obtained. It may also be possible that based on the quality factor, some input neurograms are discarded as they may contribute to inappropriate state parameters.

Programmer's Interface

The remote neuromodulatory signal generator system in FIG. 12 can include a programmer's interface. With this type of interface, segmentation of neurograms is possible and may be used for generating the state machine representations. A state machine representation can include a set of state parameters corresponding to a synthetic neuromodulatory signal. To generate the state-space representation of a neurogram, the recorded neurograms that are input into the remote neuromodulatory signal generator system can be segmented into a sequence of states. Each state can be statistically stationary. This segmentation may be achieved utilizing several methods. In one method, human user input is utilized to identify the boundaries of sections or states within the neurogram signals that may appear to be visually statistically stationary. In this method, a user can recall one or multiple neurograms and the associated metadata stored in the repository module. The one or multiple recorded neurograms can be displayed on the monitor associated with the remote neuromodulatory signal generator system. The user can review the one or multiple neurograms along with the associated metadata and identify the boundaries of sections or states that may visually appear to be statistically stationary. In one example segmentation method, ten neurograms have been recorded and stored in the repository module. These ten neurograms have been collected under similar circumstances. As an example, these neurograms may have been collected from ten different mice before, during and after injection of interleukin-1b (IL-1b). The time of injection can be known relative to the neurogram signals. Thus, a user may examine each of the ten neurograms and visually identify regions that may be associated with the injection of IL-1b. The injection of the protein can produce a change in the neurogram that can then be visualized by the user. The user may thus identify the boundaries of the states within the neurogram where the signals may look different relative to the signals that existed prior to the injection. It is also possible that the user identifies more than one statistically stationary state within the overall time period when changes to the neurogram occurred. After identification of the ten states (or multiples of ten if more than one state per neurogram is identified), these states may be analyzed as a group and the state-space representations may be generated based on population statistics.

In a second segmentation method, an algorithm is implemented within the remote neuromodulatory signal generator system as part of the programmer's interface module that identifies statistically stationary segments within neurograms acquired in similar circumstances. The algorithm can first compare the metadata of the universe of neurograms stored in the repository, to identify a set of neurograms recorded under similar circumstances and perform the statistical analysis for each neurogram within the set. For each neurogram, the statistical analysis can result in one or multiple segments within which the statistics are stationary. As the system is performing the analysis, the segments can be arbitrarily small within the limits of the system. This following is an illustrative process for segmenting neurograms.

Automatic segmentation of neurograms can be accomplished using multiple techniques including those described below, where statistics can be computed over derived features, such as the average amplitude or the inter-pulse interval. For example, a sliding window can be used to test for stationarity using signal characteristics such as entropy and form segments at high entropy points. As another example, statistics of segments for can be tested for similarity with tests, such as the Kolmogorov-Smirnoff. As a further example, unsupervised learning approaches, such as the hierarchical Dirichlet-Process, can be used to sample over segmentations and cluster time windows into longer segments with common statistics. As one example, extrema in signal characteristics, such as to amplitude, firing rate, or other derived features, can be used as structural "anchors" for segmentation (e.g., to provide knot points for splines) and multi-neurogram analysis.

Subsequent to finding segments that have similar structure, these segments can be averaged to generate a normalized segment. In one technique to generate a normalized segment, corresponding points in multiple neurograms can be identified, such as feature extrema. The time state parameter for each neurogram can be deformed to a common time reference. Any feature derived from each neurogram can then be transformed to that time reference and used to compute synthesis state parameters, such as the firing rate for a state in a state-machine model, by averaging or applying machine learning methods.

For aggregation, statistical learning over many examples can be accomplished using machine learning methods including, but not limited to Conditional Random Fields, hidden Markov models, hidden semi Markov models, and Long-Short Term Memory networks.

In a third method, human user input is used to guide performance of the process that may run on the remote neuromodulatory signal generator. As an example, the user may be able to identify the rough boundaries of the segments so that the machine performs a more accurate analysis. The rough boundaries can be the rough start and stop time of the stationary segments. In this method, just as in the previous method, for each neurogram the statistical analysis can result in one or multiple segments within which the statistics are stationary. Also, just as in the previous method, since the remote neuromodulatory signal generator system is performing the analysis, the segments can be arbitrarily small within the limits of the system.

In one embodiment, the temporal information associated with the neurogram signals and stimulus signal is known and has been recorded. In other words, in the example of the injection of IL-1b, the time when the individual spikes occur along with the time that the injection was delivered are both known.

Although FIG. 12 shows one local neuromodulatory signal generator system communicating to one remote neuromodulatory signal generator system, in some embodiments multiple local systems can be communicating to one remote system. The communication can be in various forms, such as wireless communication, wired communication, or a combination of both.

Multiple methods can be used for segmentation. For example, segmentation can be based on hand segmentation. With mouse, a user can identify state intervals by press-drag-release. Everything else is a transition, which can be automatically computed. As another example, segmentation can be based on point-and-click state recognition. A user can click on "seed" point, state is inferred or learned from information around that point. Hidden semi-Markov Models (HsMMs) are Markov models with explicit durations. In one example, HsMM learning methods can be used to segment neurograms to help create state machine models.

After defining states, the result might still be missing components. State representations can be considered as classifiers and can be used to score the probability that a set of spikes belongs with that state. The score can be a basis for removing spikes that do not belong to the state. Then the residual, remaining spikes can be used to generate a new, parallel state machine description. As an example of a residual method for neurogram modeling, states can be considered generative statistical models. Each state and/or transition can be used as a classifier for spikes. Given one neurogram, a multi-state-machine model can be derived based on the pseudocode below.

Set k=1 and iterate:
1. A user identifies state intervals and creates a state machine $S_k$.
2. NDE classifies spikes using the S and marks all spikes that are "explained well" by Sk.
3. Remove marked spikes from consideration.
4. While there are remaining spikes (not well-explained by $S_k$) increment k and go to 1

The set $\{S_k\}$ now contains a more thorough description of the input neurogram. In one embodiment, the above pseudocode is applied to multiple recordings to refine the state machine.

Neuromodulatory Signal Parameters Development Environment

A tool for determining synthetic neuromodulatory signals from neurograms can be implemented using any computer programming languages and tools. In one example, Python can be used to implement such tool. In one embodiment, state parameters or descriptors of a state can include a waveform, amplitude distribution with mean and variance, and a mean firing rate with variance. State parameters or descriptors of a state can also include parameters on how a transition between a preceding state and the state being described or a transition between the state being described and a subsequent state should occur.

The generation of a NMS can be probabilistic or deterministic. For example, for a deterministic NMS, a NMS can be generated or synthesized given identical NMS state parameters. As another example, for a probabilistic NMS, different NMS can be generated using an identical set of NMS state parameters. Such probabilistic generation can be a result of the variance in amplitude distribution and the variance in mean firing rate. In one embodiment, the parameters for describing transitions between states and include durations and averaging methods and parameters. The transitions can be deterministic, probabilistic, or conditional. For example, a conditional transition from the state being described to a subsequent state can be different depending on the properties of the subsequent state.

Figure 13:
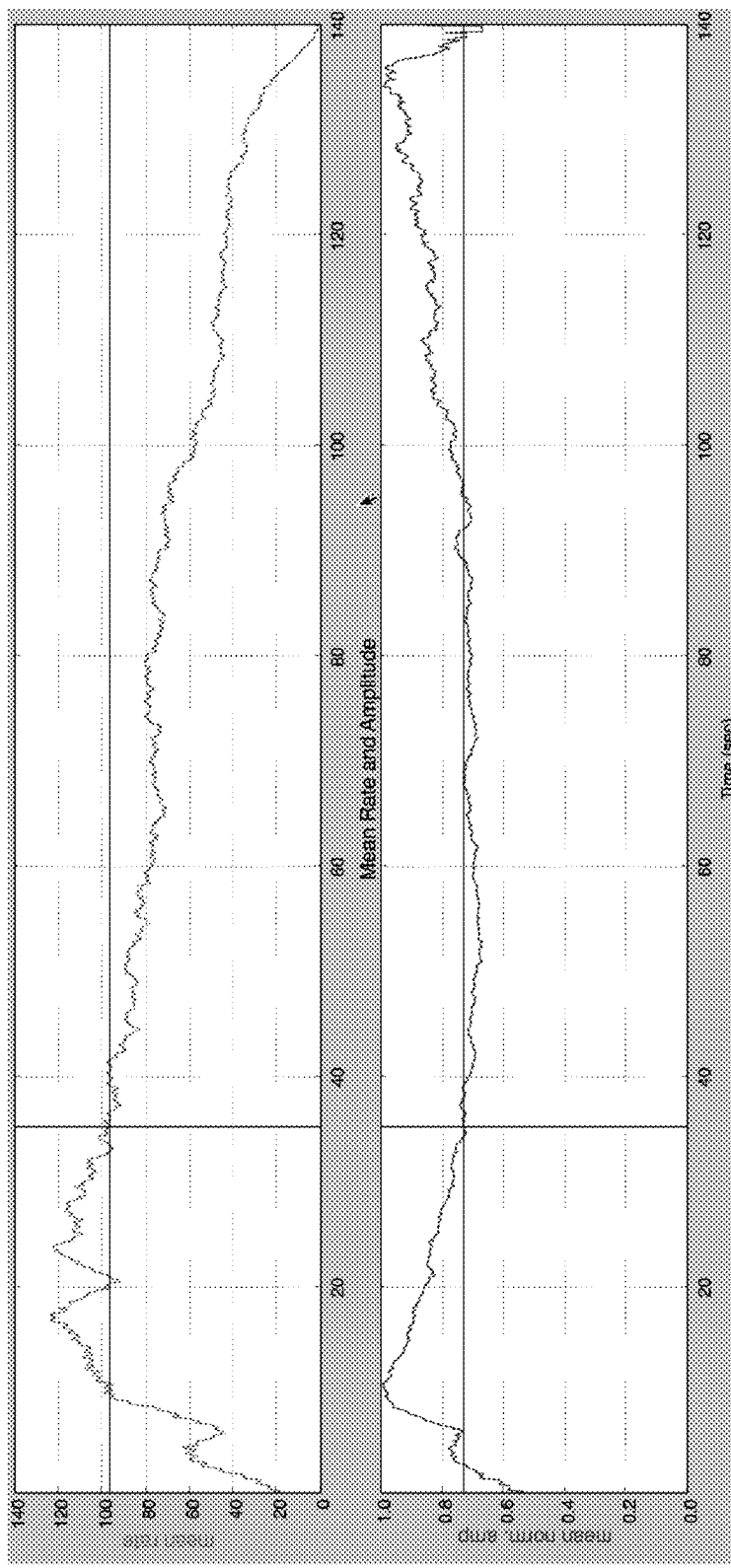
FIG. 13 shows one embodiment of an exemplary NDE screenshot before editing.
Figure 14:
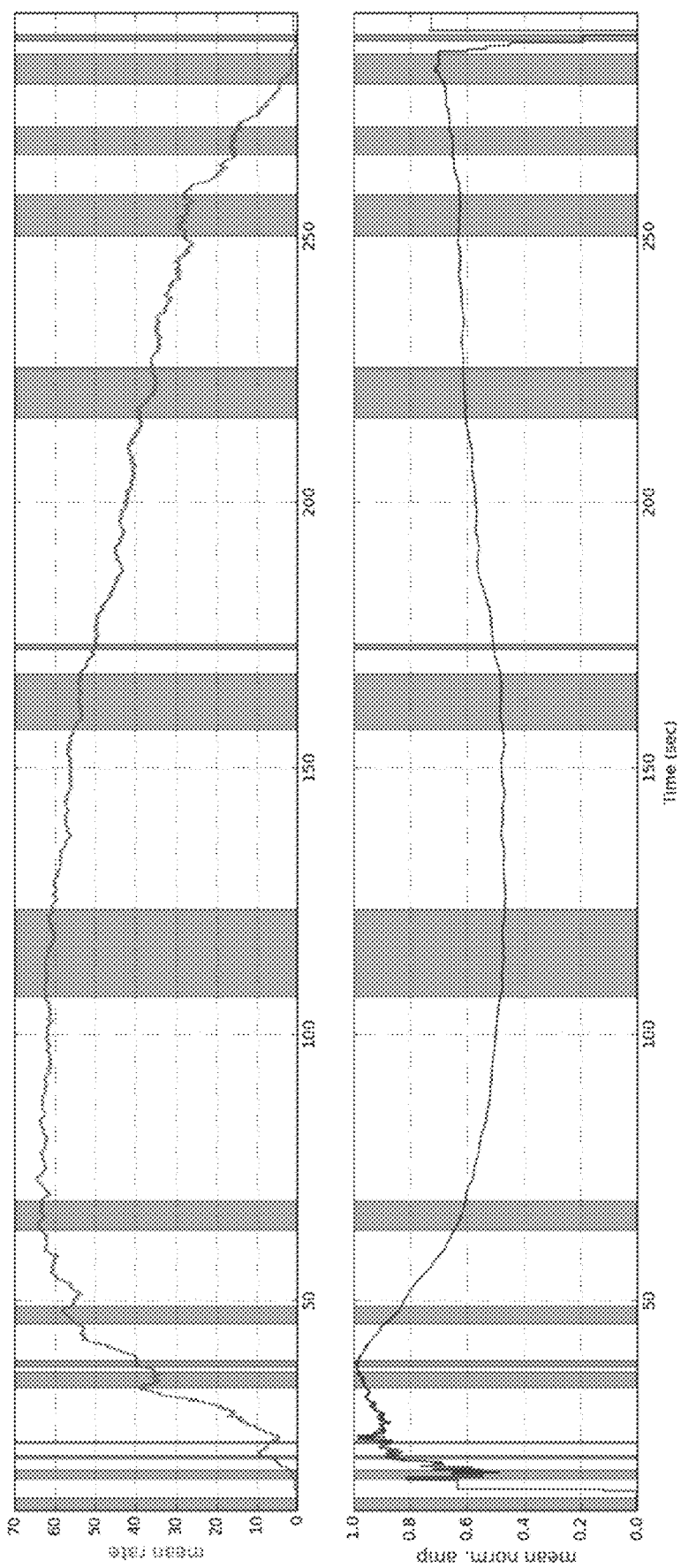
FIG. 14 shows one embodiment of an exemplary NDE screenshot after editing.

FIG. 13 shows an example NDE screenshot before editing. The example screenshot can display an interactive raw neurogram recording to a user. The display can include mean firing rate (top) and mean normalized amplitude graph to a user (bottom). The crosshairs shown allow the user to select intervals that correspond to states. FIG. 14 shows an example NDE screenshot after editing. A user can identify states (shaded), and the NDE can compute state parameters and save the state machine descriptor usable for synthesis. FIG. 15 shows an example state machine description for TNF-a signal.

Analyzer

Referring to FIG. 12, once the one or multiple states in one or multiple neurograms have been identified, an analyzer can generate the state machine representation of the neurograms. The analyzer can be implemented as an analyzer module. There are multiple ways the analyzer module may work. In one method, if multiple neurograms are present, the analyzer finds similar states across the multiple neurograms. Similarity in states may be determined based on temporal information. Using the earlier example of the ten neurograms collected under similar circumstances such as before, during and after injection of IL-1B, signals that exist in each neurogram for 5 mins after the injection can be analyzed and parametrized as one state. For example, the signal is statistically stationary for the duration in each neurogram. Similarly, signals that exist between 7 mins and 10 mins can be analyzed and parametrized as a second state. The time of 5, 7 and 10 mins are arbitrarily chosen for the purposes of illustration and are not intended to be limiting. As described herein, these boundaries can be determined by the stationarity property. Once similar states across multiple neurograms have been identified, the analyzer can generate the state machine representation for each state and for each neurogram. The state machine representation can be a set of state parameters that can include waveform parameters and their variability.

Next, an average of each state parameter can be found for each similar parameter across the multiple neurograms. Returning back to the example of the ten neurograms above, each of the ten neurograms can contain five states numbered states 1 through 5. As illustrated in FIG. 3A, each state can be represented by one or multiple state parameters. Taking the inter-pulse timing and its variability as an example, the analysis module would find the value of the inter-pulse timing and its variability for State 1 for each neurogram. The analyzer can then find the average of the ten values of the timing and the ten values of the variability to come up with two values. This process can be repeated for all the state parameters, for all the states and for the set of neurograms. At the end of this process, the neurogram may then be modeled as a sequence of states, where each state is represented by a set of state parameters and where each state is statistically stationary.

Local Neuromodulatory Signal Generator System

In one embodiment, the local neuromodulatory signal generator system (FIG. 11) accepts information from the remote neuromodulatory signal generator system. The local system can modify the NMS generated from NMS state parameters and output a synthetic neuromodulatory signal to an applicator according to the needs and desires of a subject. The applicator can be a device that ultimately applies signals to the subject. The applicator can use one or multiple technologies including electromechanical technologies, optical technologies, electrical technologies and acoustic technologies.

Figure 16:
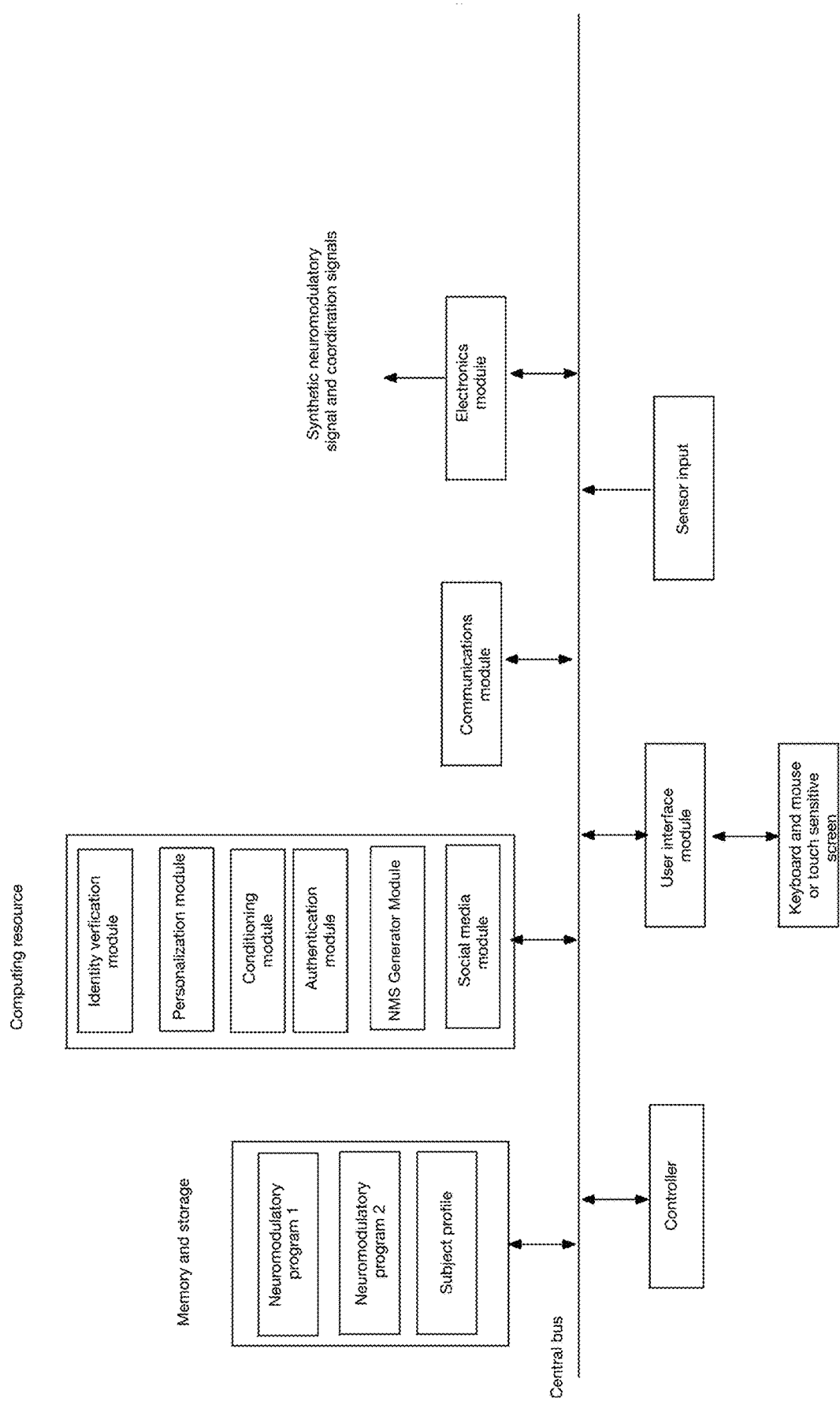
FIG. 16 is a functional diagram showing an example local neuromodulatory signal generator system.

The local neuromodulatory signal generator system is local in the sense that it is in the near vicinity of a subject. The local neuromodulatory signal generator can be configured in multiple ways, including as an application running a smartphone, as an application running with a computer. It may also be configured as an independent stand-alone device. Regardless of the configuration, the local neuromodulatory signal generator system can be implemented by a computing system, such as a mobile device, with computing resource and memory for performing the necessary computations. FIG. 16 illustrates one possible configuration of the local neuromodulatory signal generator system where it is configured as a stand-alone system. In this configuration, there may be a central bus that is responsible for transferring data and control between different modules. Components within the local neuromodulatory signal generator system that may be electrically connected to the central bus can include a memory and storage module, a computing resource where one or many modules may be executed, a communications module, an electronics module, a controller, a user interface module and a module that accepts data from external sensors. The user interface module can be in communication with a touch sensitive UI screen or other type of UI input (e.g., stylus, buttons, etc . . . ) through which the user may interact with the generator system. The function of some of these modules is provided below.

In one embodiment, through the user interface module, a subject desiring a certain effect within his or her body, uses the local neuromodulatory signal generator system to request neuromodulatory signals from the remote neuromodulatory signal generator system. The subject can be a human subject, for example. If such neuromodulatory signals are available, then a "neuromodulatory signal program" can be sent to the local neuromodulatory signal generator system. The neuromodulatory signal program can contain the NMS state parameters that describe the one or multiple states along with control data that contains information about how the neuromodulatory signal may be used. Once the desired one or multiple neuromodulatory signal programs are loaded within the memory and storage unit of the local neuromodulatory signal generator system, then according to the needs and desires of the subject, the neuromodulatory signals can be modified and applied through the applicator. A neuromodulatory signal program can contain the digital representation of the neuromodulatory signals. The computing resource illustrated in FIG. 16 can include a personalization module that is configured to modify the neuromodulatory signals in the digital domain. Once all the modifications are made, the computing resource can send the digital signals to the electronics module. The electronics module can, according to the type of applicator being used, convert the digital domain to the analog domain through the use of one or more digital to analog converters. The applicator can then apply the analog signals to the subject. In some embodiments, the local NMS generator system can receive NMSs generated by the remote NMS generator system. The NMS received can be in digital format or analog format.

User Interface (UI)

The user interface module provides a way for the user to interact with the neuromodulatory signal generator system. For example, the user interface module is one way the subject interacts with the neuromodulatory signal generator system. The subject may use the user interface module to accomplish multiple tasks, such as requesting a neuromodulatory signal that when applied to the subject can elicit a certain type of response within the body, starting the process of application and to enter feedback during or after application of the neuromodulatory signal.

In one embodiment, the user interface module can be utilized to generate a neuromodulatory signal. This request may be conveyed to the remote neuromodulatory signal generator system. If such a neuromodulatory signal exists, then the state parameters can be transferred to the local neuromodulatory signal generator. The transfer can be very quick as only the state parameters of the states are transferred to the local neuromodulatory signal generator and not the entire neuromodulatory signal.

The user interface module can also be used to start the process of application of the neuromodulatory. The subject can activate some type of control that may start the application process. The control can be a physical button or it may be a location on a touch screen.

The user interface module may also be used to provide feedback. As an example, if a neuromodulatory signal to reduce appetite is utilized, the subject can enter the feedback about how well the neuromodulatory signal worked. This feedback can be sent back to the remote generator system. All feedback associated with a specific neuromodulatory signal can be analyzed and changes to the neuromodulatory signal can be made based on the feedback. As an example, if the initial recommendation for the application time for the appetite reduction neuromodulatory signal was 20 mins and if the feedback from multiple subjects that the appetite has not suppressed enough, then the appetite reduction neuromodulatory signal can be adjusted to have an application time of 25 mins.

In another use of the user interface module, the subject can use it enter his or her profile. The profile can be entered as a response to a questionnaire that can be displayed on the UI screen. The information in the profile can be stored in the memory, and storage module can be used to personalize the sessions. The term "sessions" can refer to the process of applying the neuromodulatory signal signals to the subject.

Neuromodulatory Signal Generator

The neuromodulatory signal generator can take the state parameters of each state and convert them into a digital representation of the neuromodulatory signal. A neuromodulatory signal generator module can implement the neuromodulatory signal generator. In one example, a state is represented by eight parameters, mean inter-pulse time, one standard deviation of the inter-pulse time, mean amplitude, one standard deviation of the amplitude, mean total duration of the state, one standard deviation of the total duration of the state, a basic Gaussian pulse shape and the standard deviation of the basic pulse. Given this set of parameters, the generator module can first choose a sampling rate, such as 200 MHz and generate values for every $1/200*10^{\wedge}(-6)$ s. To generate values, the basic shape with its inherent standard deviation can be generated towards the beginning of the duration of the state. The amplitude of the basic shape can be chosen such that it conforms to the specified mean and standard deviation of the amplitude. The timing of the next pulse can be chosen such that it conforms to the specified mean and standard deviation of the inter-pulse timing. This process can be repeated for the duration of the state, which can be chosen so that it conforms to the specified mean and standard deviation of the total duration. When this process is complete, a digital representation of a series of pulses each with the basic shape is obtained such that the inter-pulse timing, the amplitude, and the total duration have similar statistical properties as a set of recorded neurograms.

The values between the states can be zero or non-zero. In one embodiment, the neuromodulatory signal generator module can fill in the neuromodulatory signal between states. In FIG. 3A, the dashed lines along the X-axis represent time segments between states. In the synthetic neuromodulatory signal, these transition states can be modeled in several ways. In one example, the values of the parameters are interpolated between the last value of the previous segment and the first value of the next segment. Each parameter can be interpolated separately. Multiple types of interpolation can be used, including linear and cubic.

Personalization

A personalization assistant can allow aspects of the sessions to be adjusted by the subject. A personalization module can implement the personalization assistant. Aspects of the sessions that can be adjusted include allowing the subject to choose operational parameters, such as the frequency, the duration and time of commencement of the sessions. The freedom to choose these aspects may be implemented by all neuromodulatory signal programs. As an example, the appetite control neuromodulatory signal program can allow all the choices of operational parameters, but the blood sugar control neuromodulatory signal program may not provide one or all the choices of operational parameters. The control data associated with each neuromodulatory signal program can provide specific instructions to the local neuromodulatory signal generator system, based on the selected operational parameters. Referring back to the example of the appetite control neuromodulatory signal program, the control data associated with this program can specify that the particular operational parameters relating to choices of frequency, duration and time of commencement that are made available to the subject. Thus, when the subject chooses this program, the controller within the local neuromodulatory signal generator system can interpret the control data, display the three possible operational parameters to be selected by the subject, and allow the synthetic neuromodulatory signal to be output via the electronics module. On the other hand, the blood sugar control neuromodulatory signal program may not allow the choice of duration. As this choice would not be specified in the control data associated with the appetite control program, the choice would not be available to the subject.

Along with the capability to provide some operational parameter choices with regard to the sessions, this module can also manage the scheduling of multiple different sessions. As an example for a diabetic patient, the appetite control program and the blood sugar control program if applied together may present inherent risks to the subject. Thus, knowing the profile of the patient, the personalization module can block the use of the appetite control program. Such blocking can be accomplished by establishing rules that can be described within the control data of each neuromodulatory signal program. The control data may, for example, specify that if a patient has a certain profile, then certain choices may be disallowed. The control data can also specify other details, such as the combination of programs that are allowed or the minimum time between sessions.

In another aspect, the local neuromodulatory signal generator system accepts input from sensors that may be coupled to or used by the subject. Based on the data received from the sensors, the sessions can be modified. In one example, the frequency of the sessions that controls appetite can be modified according to the weight of the subject. Continuing with this example, for an overweight subject with a body mass index (BMI) between 25-30, the appetite control program may be allowed only twice a day. However, for an obese subject with BMI of between 30 and 35, this program may be allowed four times a day. At the same time if a subject has a BMI of 19 or below, the appetite control program may not be allowed at all. In this case, the control data associated with the appetite control program can contain information that when interpreted by the controller, displays information in the UI screen instructing the subject to stand on a weight scale. The control data may also contain information about how frequently the subject has to weigh himself or herself. The weight can be entered manually or electronically. For example, the personalization module can receive the weight scale outputs digitally. If the weight data is not entered, then the controller can disallow the session.

Neuromodulatory Signal Conditioning

A neuromodulatory signal conditioning module allows the conditioning of the neuromodulatory signals depending on the type of applicator that is being used. For example, conditioning includes modifying the frequency content of the digital signals, increasing the amplitude of the digital signals and modifying the duration of the states according to the type of applicator. If the applicator is an acoustic device, such as a speaker, then the amplitude of the neuromodulatory signal signals can be set for example to 90 dB. This information can be contained in the control data and interpreted by the controller. If the controller detects a speaker or knows that a speaker is being used to deliver the neuromodulatory signal signals, then according to the information contained in the control data, the neuromodulatory signals may be accordingly modified. In this case the signals are played back with an amplitude of 90 dB. Similarly, if the applicator is a lightbased device, the brightness of the light and the color of the light may be controlled according to the information controlled in the control data.

In an example of how the frequency content of the digital signals may be modified, if a speaker is used as an applicator, then certain frequencies can be enhanced. The speaker can be considered inherently a low pass filter. Thus, if certain high frequencies being present in the neuromodulatory signal are important, then these frequencies may be enhanced. There are multiple ways of achieving this. For example, the Fourier transform of the digital representation of the signal is found and appropriate modifications are made in the frequency domain. Once the changes are made, the inverse Fourier transform can be applied—this results in a modified digital representation of the neuromodulatory signal. This signal can be presented to the electronics module which then applies the signal to the appropriate applicator.

Authentication

Figure 17:
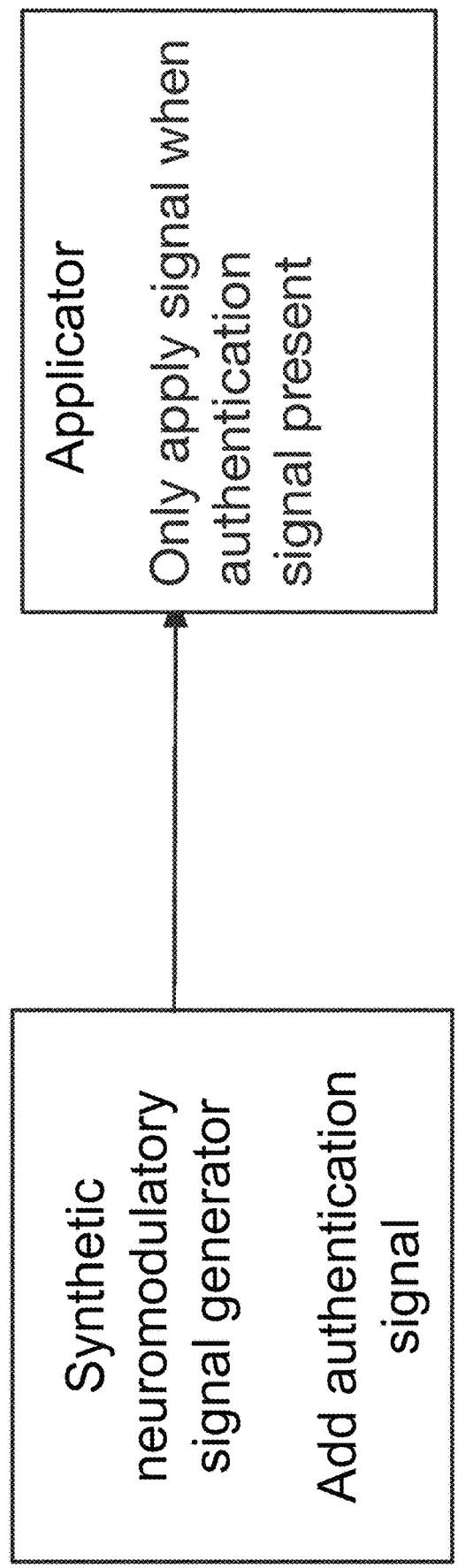
FIG. 17 shows an illustrative method for authentication.
Figure 18:
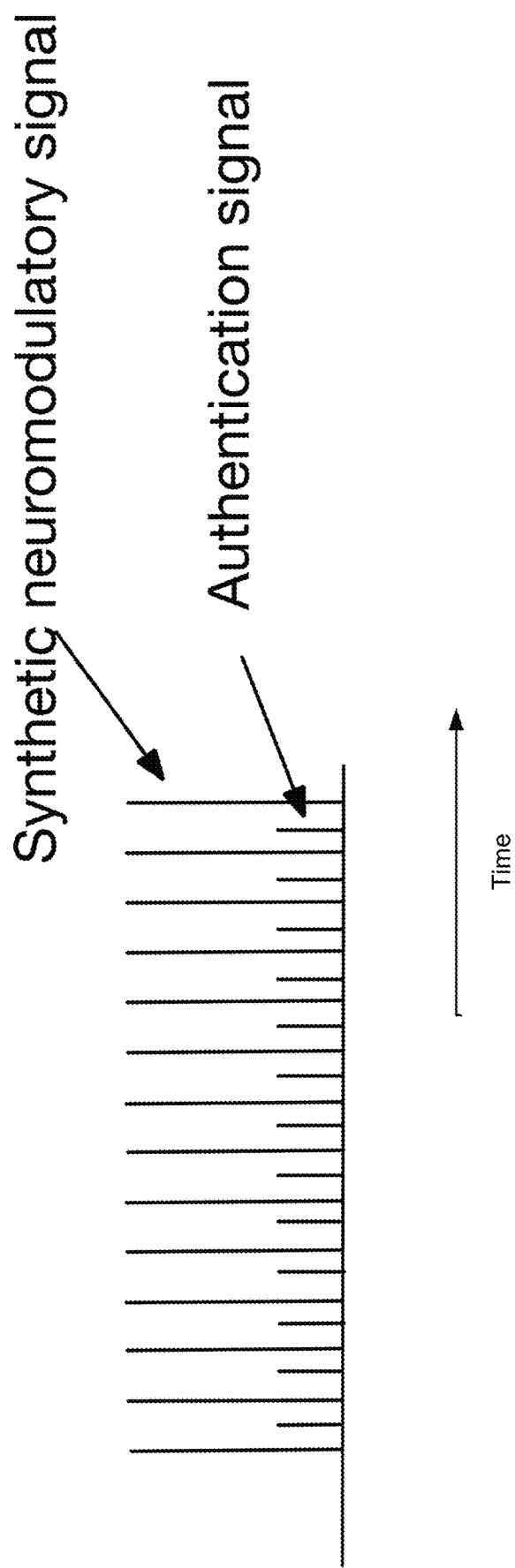
FIG. 18 is a depiction of a synthetic neuromodulatory signal and an authentication signal.

In some configurations, a synthetic neuromodulatory signal can include one or more authentication signals to prevent unauthorized modification or misuse or to prevent copying. One technique for authentication is illustrated in FIG. 17. The tall spikes represent a section of a synthetic neuromodulatory signal. The figure shows shorter spikes in between the tall spikes—the authentication signal. An authentication module within the local neuromodulatory signal generator system can add the authentication signal to the digital representation of the synthetic neuromodulatory signal. The authentication signal can be presented to the electronics module and is sent to the applicator. On the applicator, a companion authentication module can check for the presence of the authentication signal. If the authentication signal is present, the electronics module within the applicator can covert the synthetic neuromodulatory signal from a digital representation to an analog representation for an applicator to apply the analog form of the synthetic neuromodulatory signal to a subject. In one embodiment, the neuromodulatory signal can be converted and applied unmodified as the authentication signal may be known to have no effect on the human or animal. In another embodiment, the authentication signal can be suppressed physically or electronically by the applicator, or removed or reduced by software or electronic processing before the neuromodulatory signal is allowed to be applied to the subject. Although in this example smaller spikes are included within the digital representation of the neuromodulatory signal, other techniques can be used. These other techniques can include as subtle periodic variations in signal strength, using specific pulse shapes, varying the pulse spacing, and varying the phase of the pulses, In one embodiment, an authentication signal is included in the processed NMS generated to prevent unauthorized modification or misuse of the NMS, or to prevent unauthorized copying of the NMS, as shown in FIG. 18. One illustrative technique for providing an authentication signal is illustrated in FIG. 18. As shown in FIG. 18, the tall spikes represent a section of a NMS, while the shorter spikes in between the tall spikes represent the authentication signal. The system may include an authentication circuit, e.g., in the applicator, wherein the authentication circuit enables the applicator to receive and validate a NMS generated. The authentication circuit can check to determine whether the authentication signal is present in the NMS. If the authentication signal is present, the NMS is permitted to be applied to the subject using the applicator. In one embodiment, the NMS may be applied unmodified. For example, the NMS with the authentication signal can be applied without removing the authentication signal. The authentication signal may be known to have no effect on the human or animal. In another embodiment, the authentication signal can be suppressed by physical or electronic aspects of the applicator, or removed or reduced by software or electronic processing, before the neurogram can be applied to a subject. The authentication signal may include subtle periodic variations in signal strength, pulse shape, pulse spacing, or phase, which can be used to provide authentication without end-user physiologic effect.

In another embodiment, an NMS can include an authentication signal without having the shorter spikes interspersed among taller spikes as shown in FIG. 18. For example, a NMS can include one or more minor variations in the timing of spikes, minor variations in width (duration) of spikes, minor variations in the shape of spikes, and minor variations in baseline voltage level. Minor variation in the shape of spikes can be generated such that the rising edge and falling edge of each individual spike may be slow or fast. This could be used as one or two bits of information. For example, a slow rising edge and a slow falling edge can represent the value "00." A slow rising edge and a fast falling edge can represent the value "01." A variation of the baseline voltage level can be based on small waves, rather than small spikes, along the time axis in FIG. 18

The NMS (the tall spikes in FIG. 18) can be driving some effect on the end user, such as increasing the user's appetite. The NMS can include some minor signal variations. The minor signal variations can be in the form of small spikes shown in FIG. 18 or variations in the NMS. The minor signals can be filtered out by the electronics (hardware) or software of the applicator. The minor signals can have little appreciable effect on the user's body and not filtered out. Such signal variations can encode a sequence of bits to provide a level of authenticity, analogous to a digital signature. For example, the NMS without the minor variations can be modified to include minor variations generated using a public key of a public key-private key pair. The public key can be unique to the particular applicator. The applicator can decode the information encoded in the small variations using the private key of the public key-private key pair. The information encoded in the small variations can be bits, such as a hash, a cyclic redundancy check (CRC), a digital hash, a keyed hash, or a digital signature.

Identity Verification

An identity verification module can verify the identity of the subject using the local system. If the identity is not verified, this module instructs the software to display a message or provide some type of alert along with providing messages to the other modules to cease execution. Identity can be verified using multiple techniques. In one method, the subject may be asked to participate in a registration process where some type of identifying feature, such as a fingerprint, iris scan or an image of the face, may be obtained by the local system. Subsequently, a verification process may be initiated where a $3^{rd}$ party verifies the identification provided. Various methods to provide verification may be utilized. In one example, an electronic copy of the identifying information is sent to a $3^{rd}$ party which then provides an electronic verification. In another method, a physical verification is provided by a $3^{rd}$ party which then enters a unique code in the local system that allows the sessions to continue. The local system can be a portable device such as a smartphone. Once an initial verification is made, when the subject needs to apply the signals to his or her own body, the subject may need to provide some information, such as a fingerprint or be willing to provide an iris scan, or a facial scan etc., to start the execution of the sessions.

Identity verification mechanisms can also be included in the applicator. The applicator may obtain some signal from the body part that it was in contact with such as color of the skin or shape of the body part it is attached to and send this signal to the local system. To achieve this, sensors, such as miniature cameras, impedance sensors, pressure sensors, electromagnetic capacitance sensor may be included in the construction of the applicator.

Neuromodulatory Signal Generator System Configurations

Figure 19:
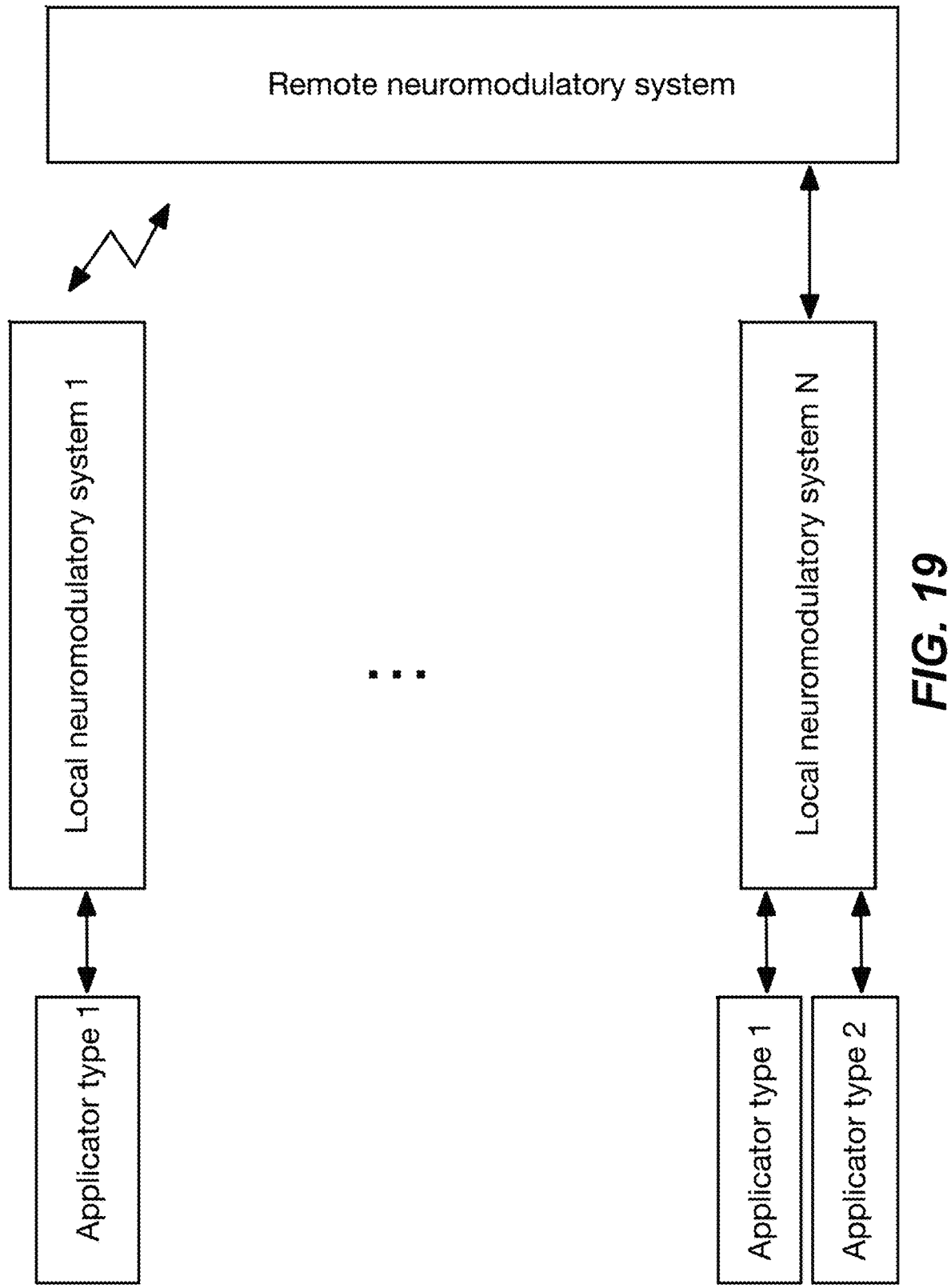
FIG. 19 is a functional block diagram of another synthetic neuromodulatory signal generator system.

While FIG. 11 illustrates one configuration, the remote system can be configured as a server in one embodiment. This configuration is illustrated in FIG. 19. This figure shows N local systems in communication with a remote system. For example, the local systems may communicate with the remote systems through a communications module that may include transceivers, processors, i/o interfaces or other components that allow electronic communication between two systems. These communications can be wireless or wired. Each local system can drive one or multiple applicator types. Thus, in this configuration, the remote system can act as a server dispensing the neuromodulatory programs to and gathering information including feedback from one or multiple subjects through the local systems. In order to serve one or multiple subjects, some other configurations are described below.

Figure 20:
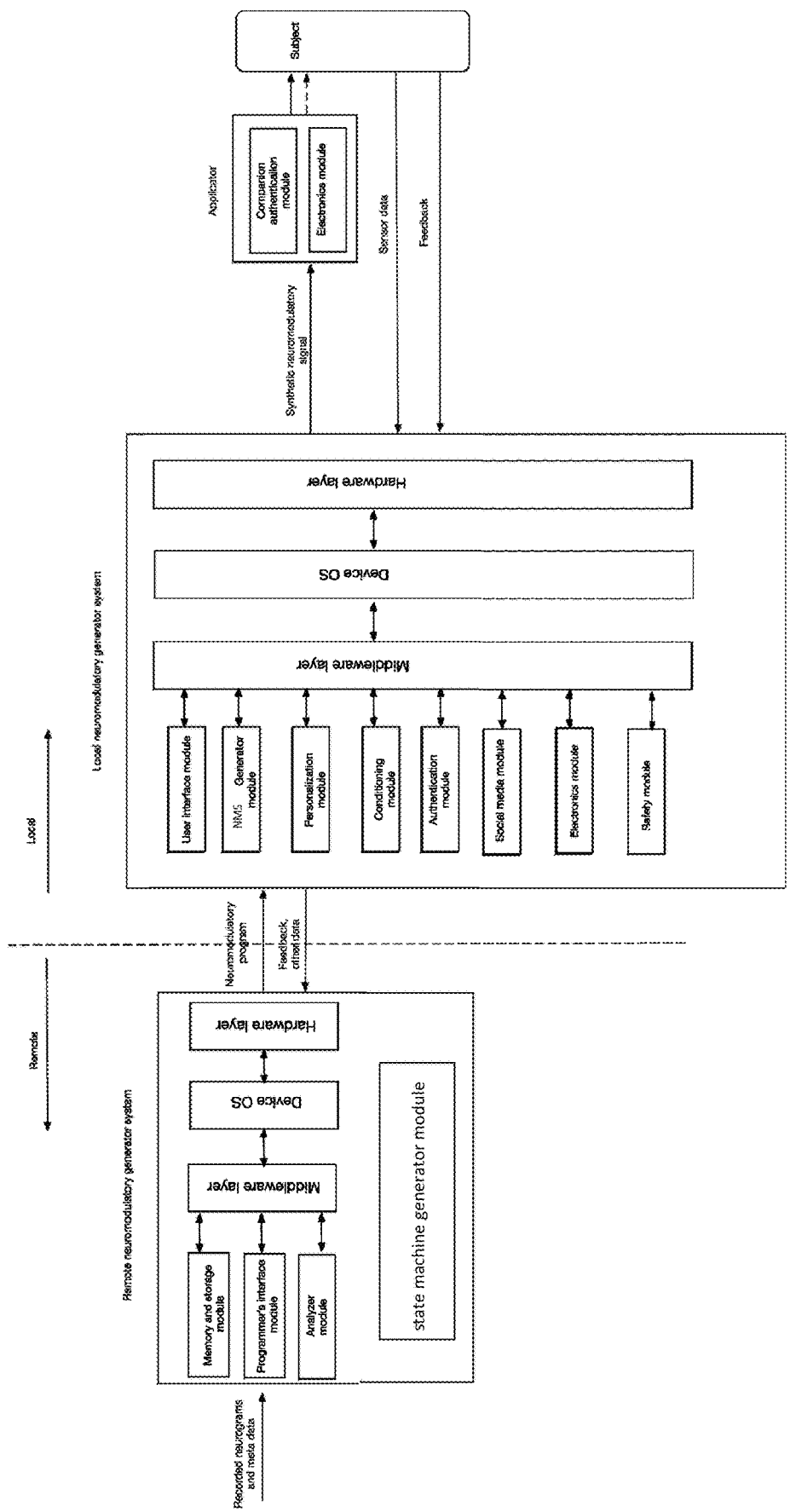
FIG. 20 is a functional block diagram of one embodiment of a synthetic neuromodulatory signal generator system with a middleware layer.

In FIG. 20 a middleware layer is illustrated according to one embodiment. The term middleware can refer to a layer of software that coordinates and supports the activity of the various modules of the neuromodulatory generator system. This layer can achieve the coordination and support by communicating to the operating system and the device drivers of the underlying computer system. This layer of software can exist within the local and the remote components of the neuromodulatory generator system. Within the local neuromodulatory generator system, as illustrated in FIG. 20, the middleware layer can be a software layer between the modules and the device operating system. In this embodiment, the middleware layer schedules the activity between the various modules. In addition, the middleware layer can generate lower level commands and communicates it to the operating system. It also communicates from the operating system up to the subject or other modules any results, messages or data as a result of execution of the commands. One example of the operation of the middleware layer is described below. In the example, the middleware layer goes through a series of steps to send a neuromodulatory signal to an applicator. The following is a non-limiting example operation of a middleware layer.

User interface module: When the subject activates the neuromodulatory application utilizing the local system, a middleware layer can initially verify the identity of the individual using the system. After the identity has been verified, the application can display messages on a display device, such as the screen of a smartphone. These messages can prompt the subject to select the type of effect that is desired, such as appetite suppression. After such selection is made, the middleware layer can check to see if the signal representation of the signal that would elicit such effect already exists within the storage of the local system. If it does, then the signal representation can be send to the neuromodulatory signal generator system. If not, the subject can be notified with some recommended actions, such as suggestions that the subject obtain the representation from the remote system.

Personalization module: After the type of effect is selected, the personalization module can perform several functions described herein. For example, this module allows the user to optimize some aspects of the sessions. In addition, it can also manage the scheduling of the various sessions for a particular user. Thus, for the effects that the personalization module determines that are allowable at the time that the subject requests the effects, the signal representation can be modified to accommodate the subject's desires. For example, the subject may want to change the duration of the session, and this is allowed for the selection the user has made.

Conditioning module: The signal representation can be further modified by the conditioning module. Since the middleware knows the applicator type, it can modify some or all of the waveform parameters. As an example, the waveform amplitude parameter of one or all states may be modified depending on the type and model of the applicator.

Authentication module: The signal representation can be yet further modified by the authentication module. As an example, to create a signal such as depicted in FIG. 17, the original state representation may need to be modified to accommodate the addition of the authentication signal. This can be accomplished in various ways including deconstructing the original states into a number of states, each with a smaller duration such that the authentication signal may be added. The authentication can be represented by states.

Neuromodulatory signal generator module: In this example, the modules described above can preserve the signal representation of the desired neuromodulatory signal. In this module, the signal representation, after all its modifications from the previous modules, is converted into a string of digital values.

Safety module: This module can perform safety checks in one embodiment. Safety checks may be performed using various techniques. For example, the state machine representation is utilized to ensure that each state by itself and in combination with other states are within safety thresholds. As an example, the waveform parameter may not be increased beyond a certain threshold. The safety module can prevent such modifications to be made. In another example, the safety module may not allow the application of a signal if the subject's medical history or other records indicate that such signals should not be applied. In yet another example, the safety module may not allow certain signals to be applied to a human if the human was below a certain age. Age data may be obtained from the records that the subject entered and subsequently verified. Further, the identification module can be continually checking the identification of the user of the local generator system so that it may be difficult for another subject or user to use that specific local system.

Electronics module: In this module, the digital representation of the signal can be appropriately processed for the applicator type. As an example, if the applicator type is a headset, then a digital to analog converter can convert the digital signals to analog signals. The electronics module can also function in a pass-through mode, if the applicator includes an analog to digital converter. For example, the digital representation may be passed through unmodified to the applicator.

In addition to the above modules, the middleware layer can interface with one or more other modules. One of these modules may be the social media module that enables users trying to elicit the same type of effect to connect with one another through well-known social media applications. This interaction with the social media module may be different as compared to the interaction with the signal processing modules in that with the social media module, the middleware layer may depend in large part with the modules already existing in the local device, such as a smart phone. In case the local system is a stand-alone device, then custom modules may be developed. Regardless of the implementation, the social media module may connect subjects trying to elicit the same type of effect. In the example of an appetite suppression application, subjects may share details of how they personalized the initial program.

The middleware layer may exist on the remote system as well. In this case, the middleware layer may interface with other types of modules, such as memory and storage module, a programmer's interface module and an analyzer module. Just as in the local system, the middleware layer can coordinate the activities of the various modules as well. Also, just as in the local system, the middleware layer can also interface between the modules and the underlying device operating system and the hardware layer.

The middleware layer can exist within the applicator system as well. Within the applicator system, the middleware layer may be responsible for several functions, such as verifying the authenticity of the neuromodulatory signal, striping the signal of the components that were added to ensure authenticity, doing the digital to analog conversion and applying the signal to the specific components. For example, the specific components can be electrodes that supply the signal to the subject's body.

In one embodiment, the middleware layer makes the neuromodulatory system hardware and device software agnostic. In an example, the local system can be based on custom hardware and software or in an android phone or an iPhone®. Regardless of the underlying hardware and device software of the local system, the neuromodulatory system can elicit the same effect. Similarly, regardless of the underlying hardware and device software of the remote system, neuromodulatory signal signals can be analyzed in similar or identical manners.

Figure 21:
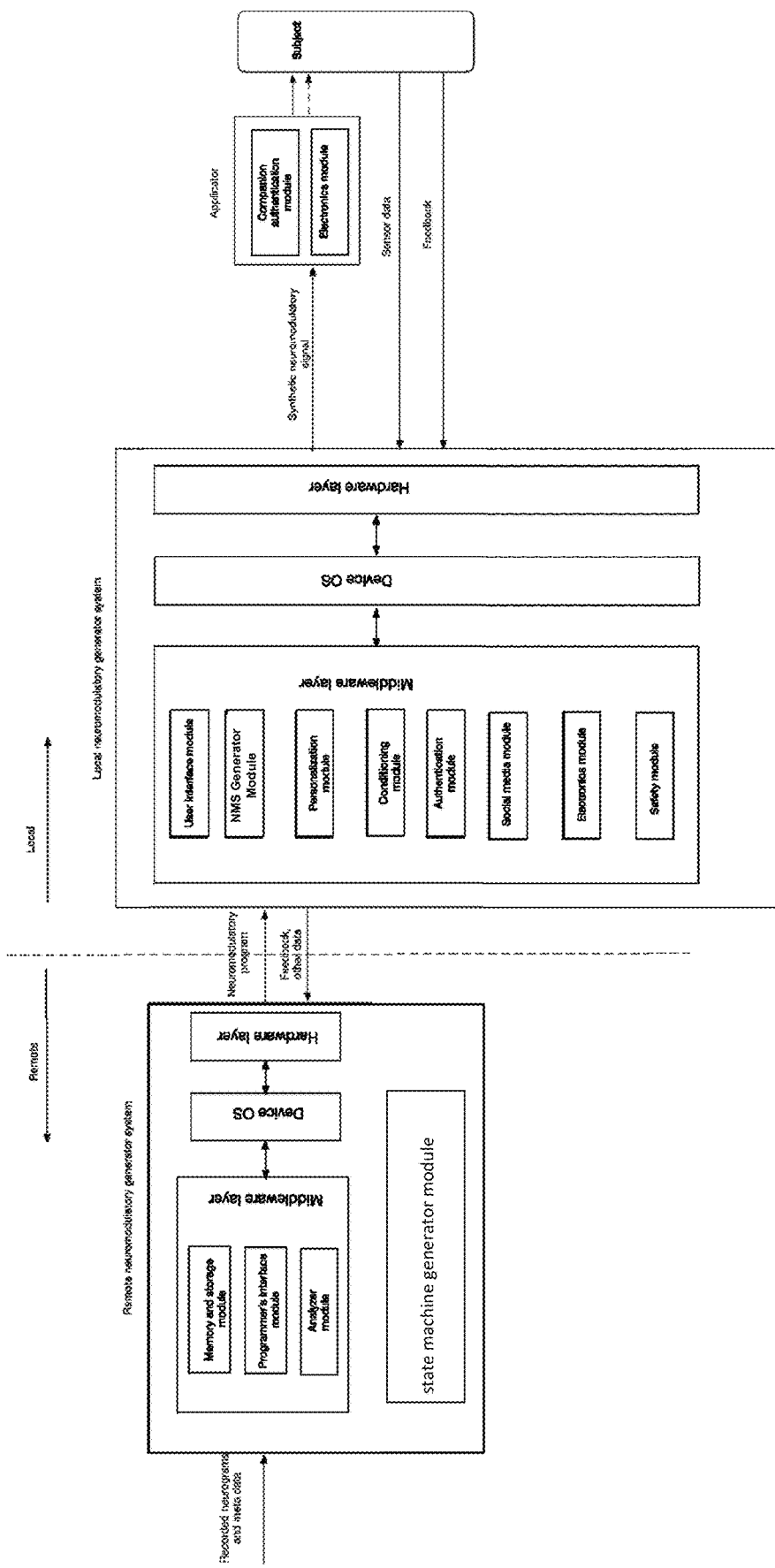
FIG. 21 is a functional block diagram of a second embodiment of a synthetic neuromodulatory signal generator system with a middleware layer.

FIG. 21 illustrates yet another configuration of the synthetic NMS generator system. In this configuration, the middleware layer can include the modules discussed earlier instead of interfacing with them. The middleware layer can still schedule activities within these modules as described earlier. While the architecture of FIG. 20 has the benefit of allowing localized changes to the modules without affecting the entire software codebase for the middleware layer, or the benefit that additional modules may be developed, the architecture of FIG. 21 can control the changes and therefore result in more stable middleware code. Either of these two architectures or a combination may be utilized according the desired flexibility of the users of the system.

Application Store

It was mentioned earlier that a subject may obtain a representation of a signal that elicits a specific effect if such representation does not exist within the local system. There may be several methods of obtaining such representation. In one method, the subject buys, retrieves, or otherwise obtains such a representation from an application store. This process may be similar to how smartphone applications are downloaded today. In one difference from that use case, the applications made available within the application store, goes through a rigorous testing and verification process. The process of making such applications available in the application store can be rigorous. The application developers may need to present information to the appropriate agency or personnel responsible for maintaining such an application store, providing evidence that the use of their applications is not harmful in any way when applied to a human. This information can include clinical data, animal data, experimental data, or data from prior use in humans. After review by the appropriate agency or personnel, the application may be made available and downloaded to the subject's local device.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The above examples, details, and scenarios are provided for illustration, and are not intended to limit the disclosure in any way. Those of ordinary skill in the art, with the included descriptions, should be able to implement appropriate functionality without undue experimentation. References in the specification to "an embodiment," "version," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated. Embodiments in accordance with the disclosure may be implemented in hardware, firmware, software, or any combination thereof. Embodiments may also be implemented as instructions stored using one or more machine-readable media, which may be read and executed by one or more processors. One embodiment may include a non-transient computer readable medium having instructions that when executed perform one of more of the functions outlined herein. A machine-readable medium may include any mechanism for storing or transmitting information in a form readable by a machine. For example, a machine-readable medium may include any suitable form of volatile or non-volatile memory. Modules, data structures, function blocks, and the like are referred to as such for ease of discussion, and are not intended to imply that any specific implementation details are required. For example, any of the described modules and/or data structures may be combined or divided into sub-modules, sub-processes or other units of computer code or data as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for applying a neuromodulatory signal to an intended target, comprising:
    a neuromodulatory signal generator system configured to generate a plurality of synthetic neuromodulatory signals, wherein each synthetic neuromodulatory signal represents at least one processed measured nerve tissue signal as a sequence of one or more states represented by one or more state parameters; and
    an electronic device is configured to communicate with the neuromodulatory signal generator system, wherein the electronic device comprises
    a user interface configured to receive a selection of at least one desired effect from the intended target;
    a library configured to cooperate with the user interface, where the library is configured to store a set of state parameters for generating synthetic neuromodulatory signals, which are derived from measured nerve tissue signals generated by neurons in a subject, for the at least one desired effect selected without application of a drug to the intended target in a safe range of parameters for that intended target, where two or more potential safe ranges of parameters are stored in the library based on different possible intended targets;
    a communication module configured to receive the selection of the at least one desired effect from the user interface and connect to the neuromodulatory signal generation system to retrieve a first synthetic neuromodulatory signal associated with the selected desired effect;
    where the user interface is configured to interact with a neuromodulatory signal generator in the neuromodulatory signal generator system, where the neuromodulatory signal generator is configured to generate the synthetic neuromodulatory signals, where the synthetic neuromodulatory signals are configured to emulate a stimulation of nerves as an alternative to drug-based treatments; and wherein application of the retrieved synthetic neuromodulatory signal to the intended target is configured to cause the intended target to experience the desired effect without application of the drug to the intended target.

2. The system of claim 1, where the library is configured to contain a set of two or more synthetic neuromodulatory signals, each set of synthetic neuromodulatory signals associated with a specific desired effect and its one or multiple states along with control data that contains information about how to apply the synthetic neuromodulatory signals to achieve the specific desired effect.

3. The system of claim 1, wherein the neuromodulatory signal generator system comprises a storage module, where the storage module is configured to receive and store a plurality of the measured nerve tissue signals produced by neurons in the subject subjected to a condition in response to application of the condition to the subject to cause the subject to experience the desired effect without application of the drug to the subject, and wherein the neuromodulatory signal generator system comprises a state machine generator module configured to communicate with the storage module to receive at least one peripheral nerve tissue signal from the measured nerve tissue signals produced by neurons in the subject, where the state machine generator module is configured to cooperate with the neuromodulatory signal generator to create the synthetic neuromodulatory signal that emulate the stored measured nerve tissue signals produced by neurons in the subject to evoke responses of the particular drug being replaced in the intended target, where the state machine generator module is configured to create the synthetic neuromodulatory signal by representing the measured nerve tissue signals produced by neurons in the subject as a sequence of one or more states, wherein each state is represented by one or more state parameters that are converted to form the synthetic neuromodulatory signal.

4. The system of claim 1, where the user interface is configured to cooperate with one or more access control mechanisms to give different types of intended targets different levels of access, where the access control mechanisms are configured to restrict access to only those synthetic neuromodulatory signals that have been approved for use for that type of intended target.

5. The system of claim 1, wherein the neuromodulatory signal generator system comprises stored operational parameters selected from the group consisting of: a) identification parameters identifying the needs or wants of the intended target; b) scheduled delivery time parameters of the first synthetic neuromodulatory signal; c) frequency of application parameters of the first synthetic neuromodulatory signal; d) parameters indicating a duration of application of the first synthetic neuromodulatory signal; and e) parameters indicating the strength of the first synthetic neuromodulatory signal, where the intended target is at least one of i) a human subject and ii) another animal subject in order to create the set of state parameters for generating synthetic neuromodulatory signals within the safe range for that human subject or that other animal subject.

6. The system of claim 1, where the measured nerve tissue signals generated by the neurons in the subject are recorded in response to stimulation of nerve tissue being applied from one or more stimulation sources consisting of at least one of i) a speaker, ii) headphones, iii) an ear bud, iv) a light emitting diode or other light-emitting device, v) a mechanical vibrator, vi) an RF transducer, and vii) a mechanical device; rather than, electrical stimulation through electrodes.

7. A method of retrieving a synthetic neuromodulatory signal to be administered to an intended target, comprising:

receiving a selection of a desired effect from a user interface of an electronic device;

downloading the synthetic neuromodulatory signal associated with the desired effect to the electronic device in response to the selection, where the synthetic neuromodulatory signal is configured to stimulate nerves as an alternative to drug-based treatments, where application of the synthetic neuromodulatory signal to the intended target causes the intended target to experience the desired effect without application of a drug to the intended target;

receiving an input of operational parameters from the user interface relating to application of the downloaded synthetic neuromodulatory signal in a safe range of operational parameters for that intended target, where two or more potential safe ranges of operational parameters are stored based on different possible intended targets, where the synthetic neuromodulatory signal to be applied was derived from measured nerve tissue signals generated by neurons in a subject, for the desired effect selected without application of the drug to the intended target in the safe range of operational parameters for that intended target, and wherein the synthetic neuromodulatory signal is applied to the intended target to cause the intended target to experience the desired effect without application of the drug to the intended target, and applying a representation of the synthetic neuromodulatory signal to the intended target of the subject according to the received operational parameters with a neuromodulatory signal generator.

8. The method of claim 7, further comprising applying the representation of the synthetic neuromodulatory signal to the intended target according to the received operational parameters in the safe range to cause the intended target to experience the desired effect.

9. The method of claim 7, wherein retrieving the synthetic neuromodulatory signal further comprises receiving at least one processed measured peripheral nerve tissue signal and creating the synthetic neuromodulatory signal by representing at least one of the processed measured peripheral nerve tissue signals as a sequence of one or more states wherein each state is represented by one or more state parameters.

10. The method of claim 7, wherein selecting the desired effect comprises selecting a desired effect from the group consisting of: anti-inflammation and pro-inflammation.

11. The method of claim 7 wherein at least one of the operational parameters is selected from the group consisting of: a) identification parameters identifying the needs or wants of the intended target; b) scheduled delivery time parameters of the synthetic neuromodulatory signal; c) frequency of application parameters of the synthetic neuromodulatory signal; d) parameters indicating the duration of application of the synthetic neuromodulatory signal; and e) parameters indicating the strength of the synthetic neuromodulatory signal.

12. A non-transitory computer readable medium containing instructions that when executed by one or more processors are configured to perform a method comprising:

receiving a selection of a desired effect from a user interface of an electronic device;

downloading a first synthetic neuromodulatory signal associated with the desired effect in a safe range of parameters for an intended target to the electronic device in response to the selection, where the first synthetic neuromodulatory signal is configured to stimulate nerves as an alternative to drug-based treatments, where application of the first synthetic neuromodulatory signal to the intended target causes the intended target to experience the desired effect without application of a drug to the intended target, where two or more potential safe ranges of operational parameters are stored based on different possible intended targets; and receiving an input of the operational parameters from the user interface relating to application of the downloaded first synthetic neuromodulatory signal in the safe range for that intended target, where the first synthetic neuromodulatory signal to be applied was derived from measured nerve tissue signals generated by neurons in a subject, for the desired effect selected without application of a drug to the intended target in the safe range of parameters for that intended target, and sending a communication to a neuromodulatory signal generator to apply a representation of the first synthetic neuromodulatory signal to the intended target of the subject according to the received operational parameters, wherein the first synthetic neuromodulatory signal is subsequently applied by the neuromodulatory signal generator within the received operational parameters to the intended target to cause the intended target to experience the desired effect without application of the drug to the intended target.

* * * * *